(12) United States Patent
Lee et al.

(10) Patent No.: US 11,217,343 B2
(45) Date of Patent: Jan. 4, 2022

(54) METHOD FOR PROVIDING ACTION GUIDE INFORMATION AND ELECTRONIC DEVICE SUPPORTING METHOD

(71) Applicant: Samsung Electronics Co., Ltd., Gyeonggi-do (KR)

(72) Inventors: No Ah Lee, Gyeonggi-do (KR); Dong Geon Kim, Seoul (KR); Kwang Yuel Ryu, Gyeonggi-do (KR); Chung Ki Lee, Seoul (KR); David Rim, Gyeonggi-do (KR); Min Hee Jang, Seoul (KR); Pravinsagar Prabakaran, Gyeonggi-do (KR); Dong Hyun Roh, Gyeonggi-do (KR); Jae Woong Chun, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 268 days.

(21) Appl. No.: 15/771,701

(22) PCT Filed: Aug. 1, 2016

(86) PCT No.: PCT/KR2016/008450
§ 371 (c)(1),
(2) Date: Apr. 27, 2018

(87) PCT Pub. No.: WO2017/073889
PCT Pub. Date: May 4, 2017

(65) Prior Publication Data
US 2018/0345081 A1    Dec. 6, 2018

(30) Foreign Application Priority Data

Oct. 29, 2015  (KR) .......................... 10-2015-0151409

(51) Int. Cl.
*A63B 24/00*         (2006.01)
*G06K 9/00*          (2006.01)
(Continued)

(52) U.S. Cl.
CPC .......... *G16H 20/30* (2018.01); *A63B 24/0062* (2013.01); *A63B 24/0075* (2013.01);
(Continued)

(58) Field of Classification Search
None
See application file for complete search history.

(56) References Cited

U.S. PATENT DOCUMENTS 5,941,837 A    8/1999  Amano et al.
6,746,371 B1   6/2004  Brown et al.
(Continued)

FOREIGN PATENT DOCUMENTS

CN    101058021 A   10/2007
CN    102110191 A    6/2011
(Continued)

OTHER PUBLICATIONS

European Search Report dated Jun. 12, 2018.
Chinese Search Report dated Apr. 22, 2021.
Korean Search Report dated Aug. 30, 2021.

*Primary Examiner* — Brent A. Fairbanks
(74) *Attorney, Agent, or Firm* — Cha & Reiter, LLC

(57) ABSTRACT

An electronic device includes a sensor, a processor, and a memory configured to store at least one instruction executed by the processor, wherein the processor is configured to collect activity information on a user related to the electronic device by using the sensor, the collecting of the activity information including creating an amount of activity of the user for a specific goal or an activity engagement level for the specific goal by using the activity information, adjust at
(Continued)

least one of an output time point, an output cycle, the number of outputs, or the output contents of the activity guide information for the user to an activity guide parameter at least based on the amount of activity or the activity engagement level, and output the activity guide information created by using the adjusted activity guide parameter through an output device operatively connected to the processor.

13 Claims, 14 Drawing Sheets

(51) Int. Cl.
  *G16H 40/67* (2018.01)
  *G16H 20/30* (2018.01)
  *H04L 29/08* (2006.01)
(52) U.S. Cl.
  CPC .......... *G06K 9/00335* (2013.01); *H04L 29/08* (2013.01); *A63B 2024/0078* (2013.01); *G16H 40/67* (2018.01)

(56) References Cited

U.S. PATENT DOCUMENTS

| | | | |
|---|---|---|---|
| 6,863,641 B1 | 3/2005 | Brown et al. |
| 6,866,613 B1 | 3/2005 | Brown et al. |
| 7,070,539 B2 | 7/2006 | Brown et al. |
| 7,128,693 B2 | 10/2006 | Brown et al. |
| 7,662,065 B1 | 2/2010 | Kahn et al. |
| 8,533,620 B2 | 9/2013 | Hoffman et al. |
| 8,613,689 B2 | 12/2013 | Dyer et al. |
| 8,663,068 B1 | 3/2014 | Dyer et al. |
| 8,825,445 B2 | 9/2014 | Hoffman et al. |
| 8,827,870 B2 | 9/2014 | Dyer et al. |
| 9,011,292 B2 | 4/2015 | Weast et al. |
| 9,259,615 B2 | 2/2016 | Weast et al. |
| 9,289,649 B2 | 3/2016 | Weast et al. |
| 9,295,413 B2 | 3/2016 | Lee et al. |
| 9,314,665 B2 | 4/2016 | Weast et al. |
| 9,345,930 B2 | 5/2016 | Hoffman et al. |
| 9,375,608 B2 | 6/2016 | Weast et al. |
| 9,415,266 B2 | 8/2016 | Weast et al. |
| 9,589,445 B2 | 3/2017 | White et al. |
| 9,595,180 B2 | 3/2017 | White et al. |
| 9,616,289 B2 | 4/2017 | Weast et al. |
| 9,636,543 B2 | 5/2017 | Dyer et al. |
| 9,750,976 B2 | 9/2017 | Weast et al. |
| 9,847,038 B2 | 12/2017 | Mayou et al. |
| 9,940,846 B2 | 4/2018 | Mayou et al. |
| 9,953,542 B2 | 4/2018 | Mayou et al. |
| 10,008,127 B2 | 6/2018 | White et al. |
| 10,026,335 B2 | 7/2018 | White et al. |
| 10,034,624 B2 | 7/2018 | Crankson et al. |
| 10,183,193 B2 | 1/2019 | Lee et al. |
| 10,234,290 B2 | 3/2019 | Lush et al. |
| 10,290,228 B2 | 5/2019 | White et al. |
| 10,354,552 B2 | 7/2019 | White et al. |
| 10,366,628 B2 | 7/2019 | White et al. |
| 10,420,983 B2 | 9/2019 | Hoffman et al. |
| 10,625,117 B2 | 4/2020 | Hoffman et al. |
| 10,967,223 B2 | 4/2021 | Hoffman et al. |
| 2007/0105629 A1* | 5/2007 | Toyama ................. A63F 13/212 463/42 |
| 2007/0249467 A1* | 10/2007 | Hong ................. A63B 71/0622 482/1 |
| 2007/0260482 A1 | 11/2007 | Nurmela et al. |
| 2010/0280838 A1 | 11/2010 | Bosworth et al. |
| 2011/0082010 A1* | 4/2011 | Dyer ................. A63B 24/0075 482/9 |
| 2012/0077641 A1 | 3/2012 | Dyer et al. |
| 2013/0106684 A1 | 5/2013 | Weast et al. |
| 2013/0184613 A1 | 7/2013 | Homsi et al. |
| 2013/0185016 A1 | 7/2013 | Homsi et al. |
| 2013/0345978 A1 | 12/2013 | Lush et al. |
| 2014/0073485 A1 | 3/2014 | Dyer et al. |
| 2014/0179491 A1 | 6/2014 | Dyer et al. |
| 2014/0180453 A1 | 6/2014 | Weast et al. |
| 2014/0180454 A1 | 6/2014 | Weast et al. |
| 2014/0180455 A1 | 6/2014 | Weast et al. |
| 2014/0180456 A1 | 6/2014 | Weast et al. |
| 2014/0200691 A1* | 7/2014 | Lee ........................ G16H 50/30 700/91 |
| 2015/0042468 A1 | 2/2015 | White et al. |
| 2015/0042475 A1 | 2/2015 | White et al. |
| 2015/0044648 A1 | 2/2015 | White et al. |
| 2015/0118658 A1 | 4/2015 | Mayou et al. |
| 2015/0118668 A1 | 4/2015 | Mayou et al. |
| 2015/0118669 A1* | 4/2015 | Wisbey ................. A61B 5/1118 434/247 |
| 2015/0119655 A1 | 4/2015 | Mayou et al. |
| 2015/0119668 A1 | 4/2015 | Mayou et al. |
| 2015/0120317 A1 | 4/2015 | Mayou et al. |
| 2016/0129308 A1 | 5/2016 | Weast et al. |
| 2016/0151671 A1 | 6/2016 | Weast et al. |
| 2016/0240100 A1* | 8/2016 | Rauhala ................... G09B 5/04 |
| 2016/0262693 A1 | 9/2016 | Sheon |
| 2016/0314670 A1* | 10/2016 | Roberts ................. A61B 5/486 |
| 2016/0325139 A1 | 11/2016 | Weast et al. |
| 2017/0209766 A1* | 7/2017 | Riley .................... A61B 5/7405 |
| 2017/0235922 A1 | 8/2017 | Weast et al. |
| 2018/0211551 A1 | 7/2018 | Mayou et al. |
| 2018/0315338 A1* | 11/2018 | Won ....................... H04B 1/385 |
| 2019/0186919 A1 | 6/2019 | Lush et al. |

FOREIGN PATENT DOCUMENTS

| | | |
|---|---|---|
| CN | 103364007 A | 10/2013 |
| CN | 104080402 A | 10/2014 |
| EP | 1 847 304 A1 | 10/2007 |
| EP | 2 434 440 A1 | 3/2012 |
| EP | 2 682 052 A2 | 1/2014 |
| JP | 2001-346928 A | 12/2001 |
| KR | 10-2008-0103386 A | 11/2008 |
| KR | 10-2012-0014471 A | 2/2012 |
| KR | 10-2012-0094906 A | 8/2012 |
| KR | 10-2014-0117548 A | 10/2014 |
| KR | 10-2015-0003568 A | 1/2015 |
| KR | 10-2015-0018620 A | 2/2015 |
| WO | 97/22295 A1 | 6/1997 |
| WO | 2015/021289 A1 | 2/2015 |
| WO | 2015/057713 A1 | 4/2015 |

* cited by examiner

| Delivery time | User pattern | Condition | Activity guide information |
|---|---|---|---|
| Morning | Onboarding | D% goal achieved | |
| | Low | Under D% Goal Progress | Try setting new goal |
| | Mid | ...... | Great! Keep it up~! |
| | High | 2X above goal for x days | Excellent~! Goal exceeded~! |
| | ... | ... | ... |
| Specific Time period | | | |
| ... | | | |

FIG. 5

METHOD FOR PROVIDING ACTION GUIDE INFORMATION AND ELECTRONIC DEVICE SUPPORTING METHOD

CLAIM OF PRIORITY

This application is a National Phase Entry of PCT International Application No. PCT/KR2016/008450, which was filed on Aug. 1, 2016, and claims a priority to Korean Patent Application No. 10-2015-0151409, which was filed on Oct. 29, 2015, the contents of which are incorporated herein by reference.

TECHNICAL FIELD

The present disclosure relates to provision of activity guide information related to activity of a user.

BACKGROUND ART

In recent years, the electronic devices have provided user functions for measuring and processing fitness information of the users as interests for health have increased.

DETAILED DESCRIPTION OF THE INVENTION

Technical Problem

In spite that the exercise tendencies of the users are different according to their personal tendencies, the existing user functions related to fitness provide only standardized and general exercise information. Accordingly, the exercise related user functions provided by the conventional electronic devices are hardly used.

The present disclosure provides a method for providing activity guide information and an electronic device supporting the same, by which personalized activity guide information may be provided according to the tendencies of the users.

The present disclosure further provides a method for providing activity guide information and an electronic device supporting the same, by which the repulsions of the user against an exercise function may be reduced and a goal set by the user may be stably and consistently attained by adaptively providing time points or cycles for providing activity guide information according to a state or an environment of the user.

Technical Solution

In accordance with an aspect of the present disclosure, there is provided an electronic device including a sensor configured to collect sensor information, a processor operatively connected to the sensor, and a memory operatively connected to the processor, configured to store the sensor information, and configured to store at least one instruction executed by the processor, wherein the processor is configured to collect activity information on a user related to the electronic device by using the sensor, the collecting of the activity information including creating an amount of activity of the user for a specific goal or an activity engagement level for the specific goal by using the activity information, adjust at least one of an output time point, an output cycle, the number of outputs, or the output contents of the activity guide information for the user to an activity guide parameter at least based on the amount of activity or the activity engagement level, and output the activity guide information created by using the adjusted activity guide parameter through an output device operatively connected to the processor.

In accordance with another aspect of the present disclosure, there is provided a method for providing activity guide information, the method including collecting activity information on a user related to an electronic device by using a sensor, creating an amount of activity of the user or an activity engagement level for a specific goal by using the activity information, adjusting at least one of an output time point, an output cycle, the number of outputs, or the output contents of the activity guide information for the user to an activity guide parameter at least based on the amount of activity or the activity engagement level, and outputting the activity guide information created by the adjusted activity guide parameter through an output device.

Advantageous Effects of the Invention

According to various embodiments, a repulsion of the user against use of exercise functions may be minimized and a goal set by the user may be stably and consistently attained by recognizing the exercise tendency of the user and providing adaptive activity guide information according to the recognized tendencies.

DESCRIPTION OF THE DRAWINGS

FIG. 5 is a view illustrating an example of activity guide information according to an embodiment;

BEST MODE

Figure 1:
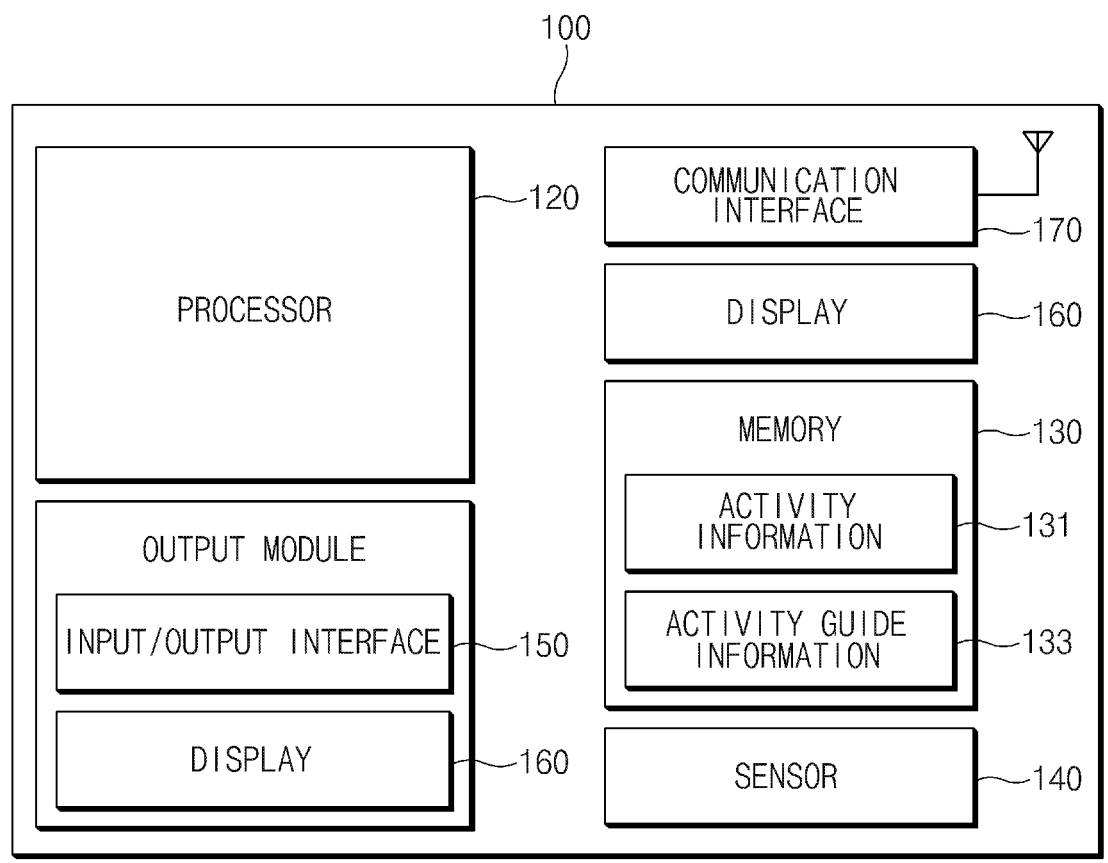
FIG. 1 is a view illustrating an example of an electronic device according to an embodiment.

Hereinafter, various embodiments of the present disclosure may be described with reference to accompanying drawings. Accordingly, those of ordinary skill in the art will recognize that modifications, equivalents, and/or alternatives on the various embodiments described herein can be variously made without departing from the scope and spirit of the present disclosure. With regard to description of drawings, similar elements may be marked by similar reference numerals.

In this disclosure, the expressions "have", "may have", "include" and "comprise", or "may include" and "may comprise" used herein indicate existence of corresponding features (e.g., elements such as numeric values, functions, operations, or components) but do not exclude presence of additional features.

In this disclosure, the expressions "A or B", "at least one of A or/and B", or "one or more of A or/and B", and the like may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used in this disclosure may be used to refer to various elements regardless of the order and/or the priority and to distinguish the relevant elements from other elements, but do not limit the elements. For example, "a first user device" and "a second user device" indicate different user devices regardless of the order or priority. For example, without departing the scope of the present disclosure, a first element may be referred to as a second element, and similarly, a second element may be referred to as a first element.

It will be understood that when an element (e.g., a first element) is referred to as being "(operatively or communicatively) coupled with/to" or "connected to" another element (e.g., a second element), it may be directly coupled with/to or connected to the other element or an intervening element (e.g., a third element) may be present. In contrast, when an element (e.g., a first element) is referred to as being "directly coupled with/to" or "directly connected to" another element (e.g., a second element), it should be understood that there are no intervening element (e.g., a third element).

According to the situation, the expression "configured to" used in this disclosure may be used as, for example, the expression "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other components. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

Terms used in this disclosure are used to describe specified embodiments and are not intended to limit the scope of the present disclosure. The terms of a singular form may include plural forms unless otherwise specified. All the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal unless expressly so defined in various embodiments of this disclosure. In some cases, even if terms are terms which are defined in this disclosure, they may not be interpreted to exclude embodiments of this disclosure.

An electronic device according to various embodiments of this disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices. According to various embodiments, the wearable device may include at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable type (e.g., an implantable circuit).

According to various embodiments, the electronic device may be a home appliance. The home appliances may include at least one of, for example, televisions (TVs), digital versatile disk (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ or PlayStation™), electronic dictionaries, electronic keys, camcorders, electronic picture frames, and the like.

According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, Global Navigation Satellite System (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, automatic teller's machines (ATMs), points of sales (POSs) of stores, or internet of things (e.g., light bulbs, various sensors, electric or gas meters, sprinkler devices, fire alarms, thermostats, street lamps, toasters, exercise equipment, hot water tanks, heaters, boilers, and the like).

According to an embodiment, the electronic device may include at least one of parts of furniture or buildings/structures, electronic boards, electronic signature receiving devices, projectors, or various measuring instruments (e.g., water meters, electricity meters, gas meters, or wave meters, and the like). According to various embodiments, the electronic device may be one of the above-described devices or a combination thereof. An electronic device according to an embodiment may be a flexible electronic device. Furthermore, an electronic device according to an embodiment of this disclosure may not be limited to the above-described electronic devices and may include other electronic devices and new electronic devices according to the development of technologies.

Hereinafter, electronic devices according to various embodiments will be described with reference to the accompanying drawings. In this disclosure, the term "user" may refer to a person who uses an electronic device or may refer to a device (e.g., an artificial intelligence electronic device) that uses the electronic device.

FIG. 1 is a view illustrating an example of an electronic device according to an embodiment.

Referring to FIG. 1, an electronic device 100 according to an embodiment may have at least one activity state (or a motion state or a movement state) while being carried or gripped by the user. The activity state, for example, may include a stop state in which there is no motion or a motion of the user is a specific reference value or less, a walking activity state, a running activity state, a cycling management state, and a vehicle use state. According to an embodiment, the electronic device 100 may collect sensor information (or sensor data) related to an activity state of the user while being mounted or held on a wrist, an ankle, the neck, or the waist of the user. Further, the electronic device 100, for example, may be realized with a portable electronic device. The portable electronic device, for example, may be realized with a mobile phone, a smartphone, a tablet PC, a personal digital assistant (PDA), an enterprise digital assistant (EDA), a digital still camera, a digital video camera, a portable multimedia player (PMP), a personal navigation device or portable navigation device (PND), a handheld game console, a mobile internet device (MID), an internet tablet, or an e-book.

The above-mentioned electronic device 100 may provide a basic setting function related to setting of a basic activity engagement level and an activity guide function related to creation and output of activity guide information based on activity information collected according to an activity state. The basic setting function, for example, may include a function of setting a program engagement level of the user according to an activity pattern for a specific time period of an early state of the activity guide program. A separate activity engagement level is not set at an initial stage of a basic setting function performance period (e.g., an initial stage of use of a program), and activity guide information according to activity information may be provided. Further, a specific activity engagement level may be temporarily set based on user information (e.g., the age, the weight, the job, the height, the fitness history of the user, and information of other users pertaining to the same group as the user). The activity guide function may include a function of providing activity guide information for a program use period after the basic setting function.

The above-mentioned electronic device 100, for example, may include a processor 120, a memory 130, a sensor 140, an output module (an input/output interface 150 and a display 160), and a communication interface 170.

The memory 130 may store at least one program related to management of the electronic device 100 or data related to management of the program. According to an embodiment, the memory 130 may store an operating system of the electronic device 100. Further, the memory 130 may store an activity guide information providing program. The activity guide information providing program may provide a goal setting function that is intended to be achieved by the user through a program, and a function of outputting state information provided in relation to attainment of a goal or various pieces of activity guide information that may endow a motive. The activity guide information providing program may provide a function of analyzing an action pattern of the user, a goal attainment pattern associated with a program, a user activity engagement level, or a progress situation based on the activity information of the user. The pattern may be used in relation to determination of activity guide information. The activity guide information providing function may provide information including various information delivery time points and various message contents.

In this regard, the activity guide information providing program, for example, include at least one instruction set (or routine, function, class, or phrase) related to a basic setting function. Further, the activity guide information providing program may store at least one instruction set related to creation of activity guide information and at least one instruction set related to output of activity guide information. Further, the activity guide information providing program may store at least one instruction set related to adjustment of a basic activity engagement level and at least one instruction set related to change of activity guide information. The instruction sets stored in the memory 130 are executed by the processor 120, and may be used for an activity guide function. The above-mentioned memory 130, for example, may be present inside or outside the electronic device 100, and may be a cloud server connected through the communication interface 170.

The memory 130 may store activity information 131 and activity guide information 133. The activity information 131 may include information on an activity zone in which sensor information of a specific level is collected, information on the kinds (e.g., walking, running, or cycling) of activities during the activity zone, and information on a non-activity zone in which sensor information of a specific level or less is collected or sensor information is not collected. The information on the non-activity zone, for example, may include information on a time point at which there is no motion of the electronic device 100, a time zone in which there is no motion, or a time point or a time zone in which a motion of the electronic device 100 is a specific level or less. Further, when sensor information is received from an external electronic device, the non-activity zone information may include information on a zone in which the sensor information is not received. The activity information 131, for example, may include pattern information that is analyzed based on the sensor information.

The activity guide information 133 may include first type activity guide information related to a basic setting function and second type activity guide information related to an activity guide function. As compared with the second type activity guide information, the first type activity guide information, for example, may be information, of which contents, an output cycle, and an output time point may be differently defined. Further, the first type activity guide information may include contents that are similar to the second type activity guide information, and may be information having contents, an expression of which are in another form. The first type activity guide information may be selected and managed according to activity information. The second type activity guide information may be selected and managed according to at least one of a basic activity engagement level, activity information, an output time point, and an output cycle.

The sensor 140 may include at least one sensor module that may collect sensor information according to an activity state of the user. For example, the sensor 140 may include an acceleration sensor and a location information collecting sensor. Further, the sensor 140 may include a passometer or a pedometer. According to various embodiments, the sensor 140 may include a sensor related to determination of a location of the user. For example, the electronic device 100 may manage a satellite navigation system based on a location information collecting sensor, such as a GPS, Glonass, or Galileo and an inertial navigation system that utilizes an angle/acceleration sensor. In relation to recognition of a location of the electronic device, a location recognizing system that utilizes telecommunication, such as 2G, 3G, 4G, or 5G, and a scheme that utilizes short range communication, such as WIRELESS FIDELITY Wi-Fi, a registered trademark), BLUETOOTH, a registered trademark, (BT), or BLUETOOTH LOW ENERGY, a registered trademard, (BLE).

The input/output interface 150, for example, may function as an interface that may transfer a command or data that are input from the user or another external device to another element (other elements) of the electronic device 100. Further, the input/output interface 150 may output commands or data received from another component(s) of the electronic device 100 to the user or anther external device. The input/output interface 150, for example, may include at least one physical button, touch button, touchpad, or touch screen. Further, the input/output interface 150 may include an input unit such as an electronic pen. Further, the input/output interface 150 may include an audio collecting device that may collect an audio signal. According to an embodiment, the input/output interface 150 may output audio information corresponding to the activity guide information or audio information corresponding to a representative activity state (e.g., walking or running) on an audio device. According to various embodiments, the input/output interface 150 may output vibration information corresponding to the activity guide information or lamp flickering information through a vibration device or a lamp.

The display 160 may be realized with a thin film transistor-liquid crystal display (TFT-LCD) panel, a light emitting diode (LED) panel, an organic LED (OLED) panel, an active matrix OLED (AMOLED) panel, or a flexible panel. The display 160 may output an execution screen according to execution of a specific application. For example, if collecting sensor information corresponding to an activity state of a specific time range or more while being turned off, the display 160 may output information corresponding to change of the activity state. According to various embodiments, the display 160 may output information corresponding to the accumulated change of the activity state in unit of a specific time period (e.g., a minute, an hour, a day, three days, a week, a month, three months, six months, or one year). Further, the display 160 may output activity guide information including at least one of a text or an image.

The communication interface 170 may form a communication channel related to performance of a communication function of the electronic device 100. According to an embodiment, the electronic device 100 may receive sensor information from an external electronic device. The communication interface 170 may deliver the received sensor information to the processor 120, and the processor 120 may collect (calculate) activity information on the received sensor information. According to various embodiments, the communication interface 170 may transmit the activity guide information to the external electronic device (e.g., a wearable device) in response to control of the processor 120.

The processor 120 may control an overall operation of the electronic device 100. According to an embodiment, the processor 120 may be realized with an integrated circuit, a system-on-chip, or a mobile AP. The processor 120 may analyze an activity state of the user by using the collected activity information based on the sensor 140 (e.g., an acceleration sensor, a passometer, or a pedometer), and may provide the activity guide information based on the analyzed activity state of the user. For example, the processor 120 may perform signal processing related to a basic setting function of setting a basic activity engagement level. Further, the processor 120 may perform signal processing for creating activity guide information and signal processing related to output of active guide information based on at least one of the basic activity engagement level determined through the basic setting function, the collected activity information, and the state of the electronic device 100. According to various embodiments, the processor 120 may perform signal processing related to adjustment of the activity engagement level or change of the activity guide information. The processor 120 may provide different pieces of activity guide information in the same situation according to the activity engagement level. Further, the processor 120 may manage activity guide information provided only at a specific activity engagement level in the same situation. In relation to signal processing, the processor 120 may include the configurations described in FIG. 2.

Figure 2:
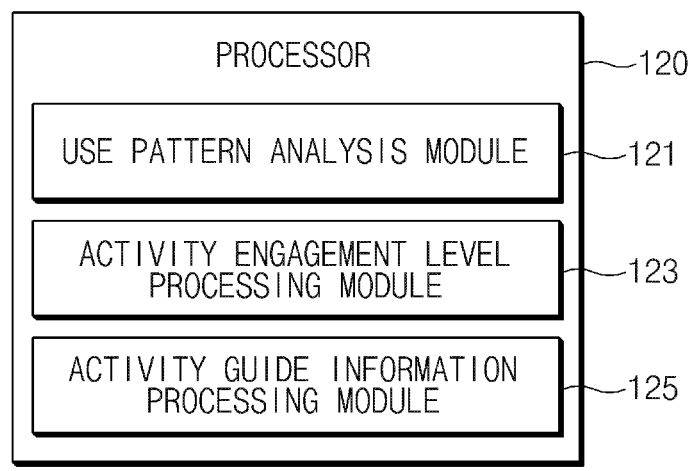
FIG. 2 is a view illustrating an example of a processor according to an embodiment.

Referring to FIG. 2, the processor 120, for example, may include a user pattern analysis module 121, an activity engagement level processing module 123, and an activity guide information processing module 125.

The user pattern analysis module 121 may collect sensor information by using the sensor 140. For example, the user pattern analysis module 121 may collect sensor information by activating the sensor 140 automatically or according to setting if the electronic device 100 is turned on. Further, the user pattern analysis module 121 may collect sensor information in real time or at a specific cycle from an external electronic device (e.g., a wearable device).

The user pattern analysis module 121 may analyze a pattern of the sensor information delivered from the sensor 140. For example, the user pattern analysis module 121 may set a window (e.g., a window that indicates a specific time range) of a specific size, and may analyze patterns of the sensor information for a time period in the set window range. According to an embodiment, the user pattern analysis module 121 may manage a window in unit of a minute, an hour, a day, a week, or a month. An hour unit window will be referenced in the following description. For example, when a 12 hour unit window is managed, the user pattern analysis module 121 may analyze pattern of the sensor information collected for 12 hours with reference to a unit of a minute or an hour. The user pattern analysis module 121 may deliver the analyzed pattern information to the activity engagement level processing module 123 or the activity guide information processing module 125.

According to various embodiments, the size of the window of the user pattern analysis module 121 may be applied in the same way in management of a basic setting function and an activity guide function. Further, the size of the window of the user pattern analysis module 121 may be differently defined according to the kind of the function (e.g., the basic setting function or the activity guide function). For example, in relation to the basic setting function, the user pattern analysis module 121 may set the size of the window to be relatively small (e.g., a unit of one hour). Further, in relation to the activity guide function, the user pattern analysis module 121 may set the size of the window to be relatively large (e.g., a unit of 6 hours) or relatively small (e.g., a unit of 30 minutes). According to various embodiments, the size of the window may vary according to the basic activity engagement level. For example, when the basic activity engagement level is relatively high, the size of the window may be set to be relatively small, and when the basic activity engagement level is relatively low, the size of the window may be set to be relatively large.

The activity engagement level processing module 123 may set a specific basic activity engagement level according to the patterns of the sensor information while the basic setting function is performed. For example, the activity engagement level processing module 123 may determine a basic activity engagement level of the user of the electronic device 100 based on sensor information for a specific time period (e.g., 7 days, 14 days, or 30 days) from an initial start time point of the user function of the present disclosure. For example, according to a goal set by the user and a goal attainment degree calculated through the sensor information, the basic activity engagement level of the user may be determined as any one of a plurality of levels (or grades).

According to various embodiments, in relation to determination of the basic activity engagement level of the user, reference values may be used. The reference values, for example, may include values obtained by dividing the set value of the goal and the set attainment degree of the goal by a plurality of engagement levels. Further, the reference values may be selected based on data (e.g., history information on the goals set by the users and history information on the goal attainment degree) of the users who use the user function. In this regard, the activity engagement level processing module 123 may receive a reference value from a server that provides information related to the basic activity engagement level reference to manage the received reference value. The server may receive information on setting of a goal and an attainment degree from a plurality of electronic device, may perform statistical grouping (e.g., grouping of data having similar characteristics) based on the received information, and may set a reference value for basic activity engagement levels corresponding to the groups. For example, the server may provide a reference value for determining to which form of group a basic activity engagement level is allocated, and may provide the reference value to the electronic device.

According to various embodiments, the activity engagement level processing module 123 may determine a basic activity engagement level of the user corresponding to the activity information collected based on a specific reference value. The activity engagement level processing module 123 may provide a training function of changing a previous reference value by using a reference value provided by the server at a specific cycle or in real time. The activity engagement level processing module 123 may provide the determined basic activity engagement level information to the activity guide information processing module 125 if the basic activity engagement level of the user is determined.

The activity engagement level processing module 123 may identify to which activity engagement level the collected activity information pertains, based on the goal and the goal attainment degree set by the user during a time period in which the activity guide function is managed. The entire activity engagement level, for example, may include a plurality of levels calculated based on the activity information and goal attainment degrees and achievements of the activity engagement levels. As described above, the basic activity engagement level may include an activity engagement level that is set based on the activity information for a specific period (e.g., a specific period at an initial stage of use of an activity guide information providing program).

According to an embodiment, the activity engagement level processing module 123 may determine that a relatively high activity engagement level is shown when the set goal attainment degree satisfies a specific condition for a specific time period or at a specific number of times. The activity engagement level processing module 123 may determine that a relatively low activity engagement level is shown when the goal attainment degree is a specific value or less for a specific time period. The activity engagement level processing module 123 may deliver an activity engagement level according to activity information to the activity guide information processing module 125.

According to various embodiments, the activity engagement level processing module 123 may adjust the set basic activity engagement level or the activity engagement level obtained during performance of the activity guide function. For example, the activity engagement level processing module 123 may adjust the set activity engagement level to the collected activity engagement level when an achievement (e.g., a goal attainment degree) of a specific value or more is maintained for a specific time period or more (e.g., 7 days or more). According to an embodiment, the activity engagement level processing module 123 may decrease the activity engagement level when the activity engagement level determined through analysis of sensor information is repeatedly created for a specific time period while being maintained at a specific value or less. Further, the activity engagement level processing module 123 may increase the activity engagement level when the activity engagement level is a specific value or more because the goal attainment degree is a specific value or more for a specific time period. When the activity engagement level is adjusted, the activity engagement level processing module 123 may automatically change the activity engagement level and then guide the change (e.g., output information on the change on a display or output audio information related to the change). Further, the activity engagement level processing module 123 may guide the change of the activity engagement level, may change the activity engagement level according to the identification of the user, or may maintain the previous activity engagement level according to the rejection of the user. According to various embodiments, the activity engagement level processing module 123 may automatically perform an activity engagement level setting function during a basic setting period again when the user function of the present disclosure is initiated.

The activity guide information processing module 125 may create activity guide information that is to be output or select activity guide information of any one of pieces of activity guide information stored in advance, based on at least one of the activity information, the pattern information (e.g., the activity engagement level to which the current activity information pertains), and the activity engagement level information, which have been received. According to an embodiment, the activity guide information 133 may include information used for the basic setting function, and information used during performance of the activity guide function. The activity guide information processing module 125 may select at least one of activity guide information related to the basic setting function or activity guide information related to the activity guide function according to the user function management state of the electronic device 100 to output the information.

According to an embodiment, while the basic setting function is used, the activity guide information processing module 125 may select activity guide information based on the collected activity information. For example, the activity guide information processing module 125 may select (or create) the activity guide information that is to be output, based on pattern information obtained by analyzing activity information during a specific previous time period, such as a unit of hour or a unit of a day, and may output the selected activity guide information. According to various embodiments, the activity guide information processing module 125 may output information (e.g., basic setting start information, basic setting residual time information, or basic setting elapse time information) on the basic setting period according to a user input or a specific scheduling time. As the basic setting function ending condition is satisfied, the activity guide information processing module 125 may output a determined basic activity engagement level if the basic setting function is ended (e.g., a specific time period passes).

The activity guide information processing module 125 may output different pieces of activity guide information based on the kind of the activity engagement level and the goal attainment degree during management of the activity guide function. For example, the activity guide information processing module 125 may differently set contents of the activity guide information that is to be output, an output time point of the activity guide information, or an output cycle according to the kind of the set activity engagement level (e.g., the activity engagement level set during the basic setting period or the activity engagement level updated during the activity guide function) and the goal attainment degree.

For example, when a relatively low activity engagement level is set for the same goal attainment degree, the activity guide information processing module 125 may output the activity guide information such that the output cycle becomes smaller. At a time point at which the output time point is inactive, the contents of the information may include contents of positive expressions for induction of fitness. Further, for example, when a relatively high activity engagement level is set for the same goal attainment degree, the contents of the information may include contents of positive expressions and negative expressions to induce fitness such that the output cycle is greater (than when the basic activity engagement level is low) at time points when the output time point is inactive and active.

According to various embodiments, an electronic device according to an embodiment includes a sensor configured to collect sensor information, a processor operatively connected to the sensor, and a memory operatively connected to the processor, configured to store the sensor information, and configured to store at least one instruction executed by the processor, the instruction executed by the processor collects activity information on a user corresponding to an electronic device by using a sensor, the collecting of the activity information includes creating an amount of activity of the user or an activity engagement level for a specific goal by using the activity information, and instruction executed by the processor is configured to adjust at least one of an output time point, an output cycle, the number of outputs, or the output contents of the activity guide information for the user to an activity guide parameter at least based on the amount of activity or the activity engagement level, and output the activity guide information created by using the adjusted activity guide parameter through an output device functionally connected to the processor.

According to various embodiments, the instruction executed by the processor is configured to identify situation information (e.g., a motion state or a non-motion state of the electronic device 100, an activity state or a non-activity state of the user, or schedule information) for the electronic device, and adjust the activity guide parameter at least further based on the situation information.

According to various embodiments, an electronic device according to an embodiment includes a processor, and a memory electrically connected to the processor and configured to store at least one instruction executed by the processor, and the instruction executed by the processor collects activity information based on at least one of collection of sensor information or a size of the sensor information, activity guide information that is to be output for the activity information based on a set goal, and at least one of an output time point, an output cycle, a number of outputs, and output contents of the activity guide information is differently output based on at least one of a motion state of the electronic device, an activity engagement level set according to a program participation level, and a current time.

According to various embodiments, the instruction executed by the processor may make the output cycle of the activity guide information relatively short when the activity engagement level is relatively high and may make the output cycle of the activity guide information relatively long when the activity engagement level is relatively low.

According to various embodiments, the instruction executed by the processor may be configured to make the number of outputs of the activity guide information relatively large when the activity engagement level is relatively high and make the number of outputs of the activity guide information relatively small when the activity engagement level is relatively low.

According to various embodiments, the instruction executed by the processor may be configured to omit output of the activity guide information if the current state is a motion state, and output the activity guide information if the current state is a non-motion state (without any motion) for a specific time period.

According to various embodiments, the instruction executed by the processor may be configured to determine whether the current state is a motion state or a non-motion state and output specific activity guide information corresponding to the determined current state.

According to various embodiments, the instruction executed by the processor may be configured to output activity guide information of different contents according to a time band (e.g., morning, afternoon, evening, or the like) to which the current time pertains.

According to various embodiments, the instruction executed by the processor may be configured to change contents of the activity guide information and output the changed activity guide information when activity guide information that is to be output has the same contents as previously output activity guide information.

According to various embodiments, the instruction executed by the processor may be configured to determine a program engagement level based on activity information during a basic setting period of the program and store the determined activity engagement level according to the program engagement level.

According to various embodiments, the instruction executed by the processor may be configured to adjust the activity engagement level according to a degree of repetitions of the activity information.

According to various embodiments, the instruction executed by the processor may be configured to decrease the activity engagement level when a size of the activity information is maintained at a specific value or less for a specific time period, and increase the activity engagement level when the size of the activity information is maintained at the specific value or more for a specific time period.

According to various embodiments, the instruction executed by the processor may be configured to analyze a pattern of the activity information in relation to creation of the activity guide information, detect a pattern at least a part of which is similar or the same by comparing the analyzed pattern and stored reference patterns, calculate estimated activity information with reference to the detected pattern, calculate a goal attainment degree by comparing the estimated activity information and the goal, and determine contents of the activity guide information based on the calculated goal attainment degree.

According to various embodiments, an electronic device according to an embodiment includes at least one of a sensor configured to collect sensor information or a communication interface configured to receive the sensor information from an external electronic device, a processor electrically connected to the sensor or the communication interface, and a memory electrically connected to the processor and configured to store at least one instruction executed by the processor, and the instruction executed by the processor collects activity information based on at least one of collection of sensor information or a value of the sensor information, activity guide information that is to be output for the activity information based on a set goal, and at least one of an output time point, an output cycle, and a number of outputs of the activity guide information is differently output based on at least one of a motion state of the electronic device, an activity engagement level set according to a program participation level, and a current time.

Figure 3:
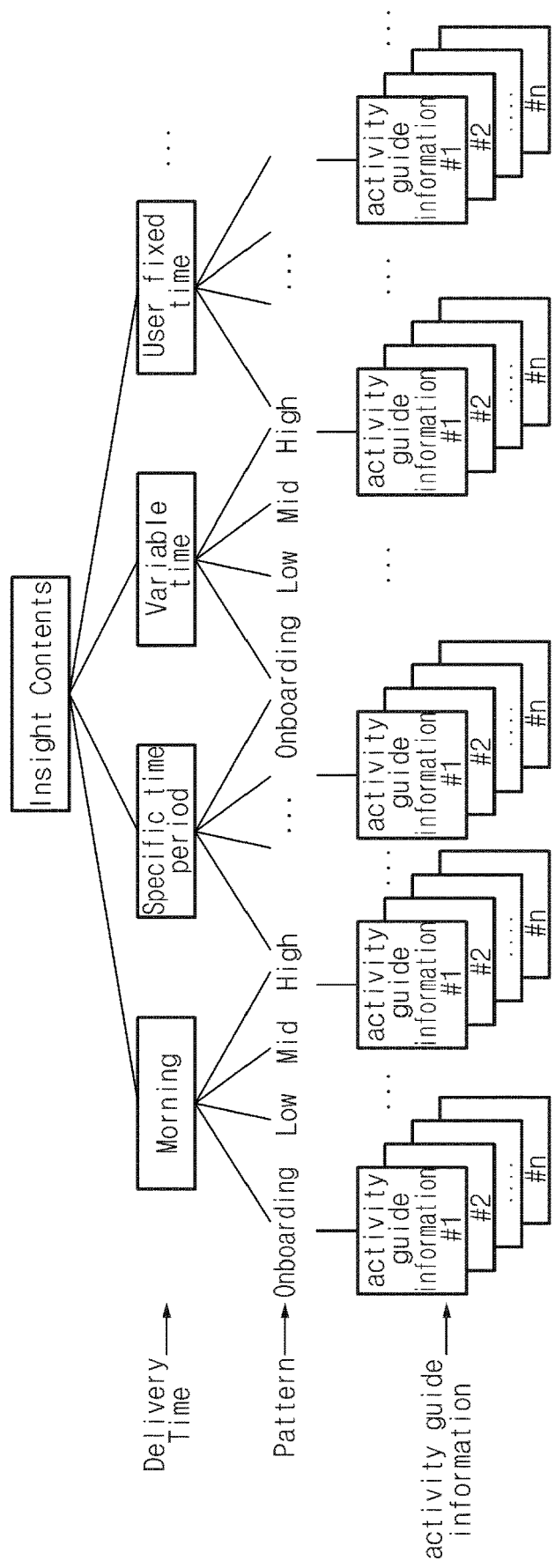
FIG. 3 is a view illustrating an activity guide information providing structure according to an embodiment.

FIG. 3 is a view illustrating an activity guide information providing structure according to an embodiment.

Referring to FIG. 3, in relation to the activity guide information providing structure, the user of the present disclosure may provide activity guide information (e.g., an insight message) for the same sensor information in various forms.

For example, the activity guide information providing structure may include an output time point (a delivery time), an analyzed user pattern, and activity guide information (an insight message) structure that is to be provided. According to an embodiment, the delivery time, for example, may include morning, a specific time period, a variable time, and a user fixed time. Further, the user pattern may include an activity engagement level (low, mid, high, etc.) of an initial stage of performance of a guide program. In the activity guide information, at least one of a plurality of contents or expressions may include another piece of message information according to the set activity engagement level or the activity engagement level pertaining to the collected activity information.

The processor 120 may analyze an activity pattern of the user based on a time point at which information is to be output to the electronic device 100 and the collected sensor information, and may determine activity guide information corresponding to the analyzed activity pattern. The activity guide information may include whether a goal set by the user is attained, activity guide information that helps attainment of the goal, reward information for the attainment of the goal, user function performance state information that is currently progressed, a program reminder, user function observation state information, monitored activity summary information, and system information delivered from a program related to the function.

According to various embodiments, the activity guide information providing structure of the present disclosure may be divided into a basic setting period corresponding to an initial stage of performance of a guide program and an activity guide function management period to be managed. During the activity guide function management period, the processor 120 may output activity guide information in various forms according to the activity engagement level (a level (e.g., high, mid, or low) classified into a program participation level and the like at an initial stage of performance of the guide program and during an activity guide function management period), the collected activity information, an output time point of the activity guide information, and the like.

The processor 120 may classify the basic setting period (e.g., a specific period corresponding to the initial stage of the performance of the guide program) and the activity guide function management period to output the activity guide information in various forms. Further, the processor 120 may adjust an output time point of the activity guide information in consideration of an activity state of the user and an initial motion time point.

During the basic setting period, the processor 120 may deliver activity guide information at a time point of attainment of a specific level (e.g., 40% or 80%) for the set goal. If the basic setting period passes, the processor 120 may additionally deliver activity guide information indicating that the user has to do his or her best for attainment of a goal if it is determined that an estimated goal attainment degree (e.g., a goal attainment possibility that is calculated based on a total activity time of the user for a day during a period from a specific time point to a current time point) is low (e.g., 20%) at a specific time point in an inactive state of the user.

The basic setting period is a designated specific time period, and may be designated to 14 days or 20 days at an initial stage of user of a program. During the basic setting period, the processor 120 may output activity guide information that is classified as information including positive contents such that the user may feel interested while a repulsive feeling to a fitness program is lowered. The processor 120 may output at least one of activity guide information classified as information including negative contents that is necessary to increase the goal attainment degree and activity guide information including positive contents if the basic setting period passes.

According to various embodiments, the processor 120 may output activity guide information in consideration of whether the action of the user is to be changed or maintained in the contents of the action guide information (in consideration of an active or inactive state of the user (by utilizing a step count, a phone usage, or the like)). For example, the processor 120 may deliver activity guide information that requires change of the action (state) of the user in a state (time point) that requires change of the action. According to an embodiment, if it is predicted that the user is in an inactive state and it is difficult to attain a specific goal in the current state, the processor 120 may deliver activity guide information of the contents that allows an action. In another embodiment, the processor 120 may not deliver activity guide information even if it is predicted that it is difficult to attain a goal at a time point at which the user in an active state. The processor 120 may use a database of contents that induce change of an action when action guide information of contents that requires change of the action is created. The electronic device 100 includes various beforehand databases (e.g., including a message of contents that request change of a state from an inactive state to an active state and a message of contents that request maintenance of an active state) for the change of the action.

For example, the beforehand database may include a message, such as Halfway! 50% of goal achieved, Almost done! 90% of goal achieved, Don't fall behind! Estimated active minutes 20 less than goal. Output condition information for at any time point the change of the action has to be output may be mapped with the messages.

According to various embodiments, when the set goal attainment fails during the basic setting period, the processor 120 may output activity guide information to which level of the goal the attainment was made at an initial motion time point of the following day. If the basis setting period passes, the processor 120 may output activity guide information on a case (e.g., 2 weeks, 2 months, or 3 months) in which the attainment of the set goal continuously failed or a case in which the attainment of the goal failed for a specific time period (e.g., one day) after the goal continuously was attained for a specific time period (e.g., 7 days) at an initial motion time point of the following morning. The processor 120 may output activity guide information on a case in which the attainment was made by twice or more of the goal for a specific time period or more (e.g., 7 days) or a case (e.g., 6 days or more for one week, 12 days or more for 2 weeks, or 27 days or more for one month) in which the attainment of the goal rarely failed at the initial motion time point of the following morning.

According to various embodiments, during the basic setting period, the processor 120 may deliver which level of the goal the attainment reached when the attainment of the goal failed yesterday to increase a motive for use of the program by the user and adapt the user to the fitness program. In order that the user does not feel bored if the basic setting period passes, the processor 120 may output activity guide information in an exceptive case of a specific level or more, such as a case in which a goal was attained almost consistently, a goal was not attained consistently, or a goal attainment level is consistently very high, without delivering an everyday feedback for a failure of attainment of a goal.

According to various embodiments, the processor 120 may recognize an initial morning motion time point of the user to output activity guide information at the corresponding time point. Then, the processor 120 may determine an initial morning motion time point in consideration of a phone usage pattern, a current time, and a step count of the electronic device 100.

According to various embodiments, the processor 120 may deliver the activity guide information related to a goal attainment degree for the previous day or a recent goal attainment situation at an initial morning motion time point that may give a motive for the user and is suitable for allowing the user to make a plan for attainment of a goal.

The above-mentioned activity guide information, for example, may include "Awesome! 98% of goals achieved in last 2 weeks.", "Goal exceeded by 200 minutes on average. Try setting new goal.", "Almost! Just 5 minutes below goal yesterday.", "Goal not achieved for 1 month (20 minutes below on average).", "Try setting new goal. Be more active and improve your health."

Figure 4:
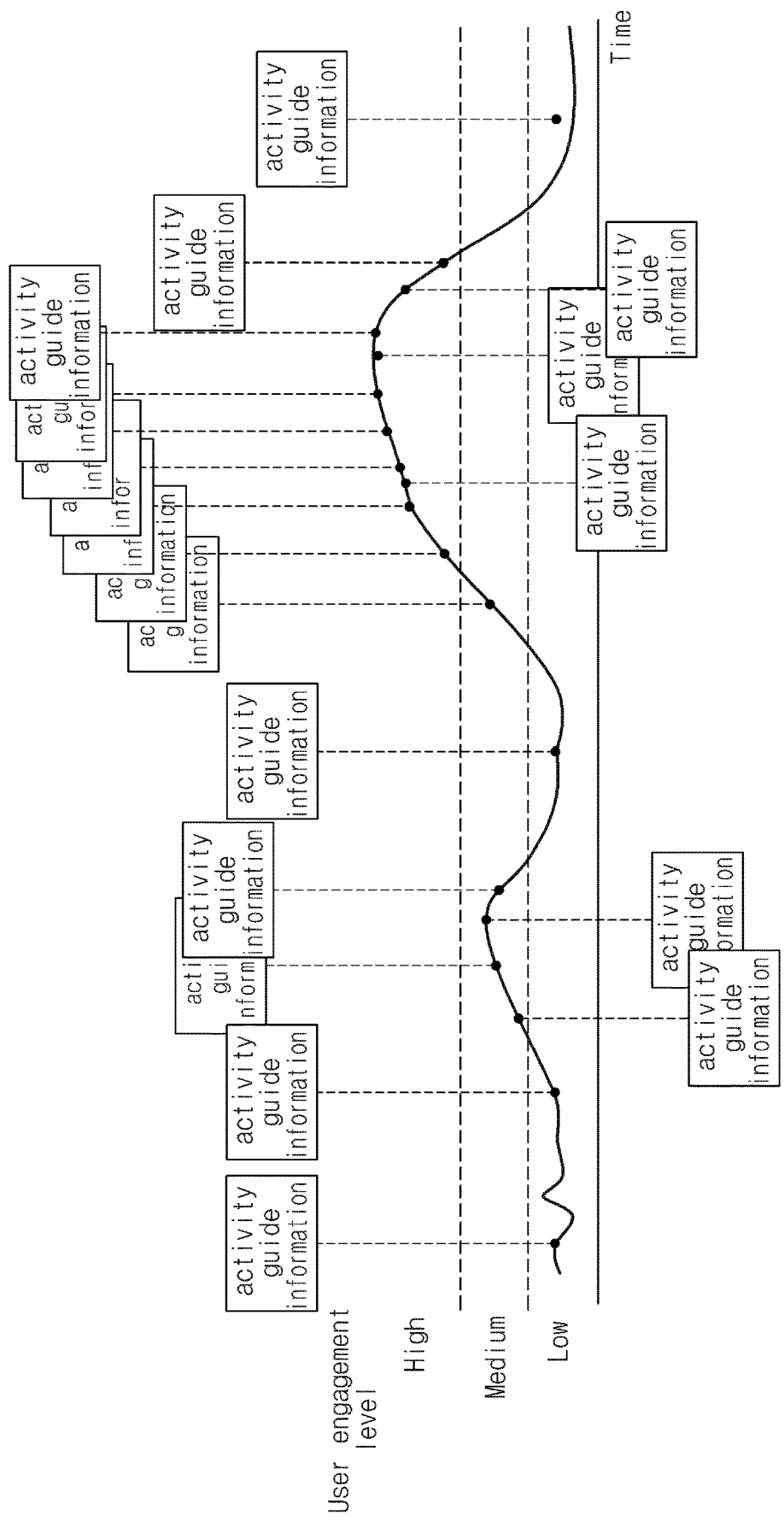
FIG. 4 is a view illustrating an example of providing activity guide information according to an embodiment.

FIG. 4 is a view illustrating an example of providing activity guide information according to an embodiment.

Referring to FIG. 4, the processor 120 of the electronic device 100 may differently give at least one of an output time point, a cycle, and output contents of the active guide information according to the activity engagement level. According to an embodiment, the processor 120 may perform processing such that the activity guide information output time point may vary according to the number of outputs of the activity guide information. For example, the processor 120 may output activity guide information a number of times that is small as compared with the case in which the number of times is large (e.g., high) when the set basic activity engagement level or activity engagement level (e.g., a level according to the program participation level of the user) is relatively low (e.g., low).

The value of the participation level, for example, may be classified into a use time or the number of uses of the activity guide information providing program. For example, the value of the participation level may be classified with reference to preset reference values, such as setting of a goal in unit of a specific time, a goal attainment degree, and the number of goal attainments.

Further, the processor 120 may increase the number of outputs of the activity guide information such that the user may be interested and motivated when it is determined that the amount of activity (or activity information) of the user during a specific time period becomes closer to the goal set by the user or the participation level (or engagement level) tends to increase based on the analysis of the collected sensor information (or by calculating activity information based on the sensor information and analyzing the calculated activity information).

As illustrated in the drawings, the processor 120 may output active guide information, the amount of which is relatively small, for the activity information of the user corresponding to a relatively low basic activity engagement level or a low activity engagement level (e.g., an activity engagement level acquired during performance of the activity guide function) analyzed through the current activity information. Further, the processor 120 may output activity guide information, the amount of which is large, for the activity information of the user corresponding to a relatively high base activity engagement level or a relatively high activity engagement level. The activity guide information used in the basic activity engagement levels or activity engagement levels may include different contents. Further, when the same activity information is collected at the same activity engagement level, the processor 120 may output new activity guide information in which at least some of the contents or expressions of the activity guide information output in relation to the previous activity information are different.

FIG. 5 is a view illustrating an example of activity guide information according to an embodiment.

Referring to FIG. 5, the processor 120 may differently set the activity guide information that is to be output according to an output time point (delivery time), an activity engagement level (user pattern), and a set goal attainment condition. Additionally, the processor 120 may also make the activity guide information different according to the basic activity engagement level to output the activity guide information. For example, the processor 120 may identify the goal attainment state based on the sensor information according to monitoring of the user. For example, an onboarding activity engagement level (basic activity engagement level) may represent a state in which D % of a specific goal is attained, a low activity engagement level may represent a state in which D % or less of a goal is attained, a middle activity engagement level may represent a state in which a goal is attained, a high activity engagement level may represent a state in which twice or more of a goal is attained for a specific time period (x days). The processor 120 may output activity guide information corresponding to attainment of D % of a goal on an electronic device 100 of an onboarding user (an initial user of a program) in the morning.

The processor 120 may output activity guide information that requests setting of a new goal on the electronic device 100 of the user that represents a low activity engagement level acquired for a specific time period in the morning. The processor 120 may output activity guide information that guides attainment of a goal for the user to which the activity information acquired for a specific time period indicates a middle activity engagement level in the morning. The processor 120 may output activity guide information that indicates an excellent amount of activity for the user to which the activity information acquired for a specific time period indicates a high activity engagement level in the morning. According to various embodiments, the processor 120 may urge a program user according to an activity engagement level (a participation level, and a basic activity engagement level or an activity engagement level) that is currently shown, may induce an interest in the program by suggesting a new goal, and may consistently maintain a program participation level. The processor 120 may output various pieces of activity guide information according to an activity engagement level to which currently acquired activity information pertains, with reference to a previously set activity engagement level in a process of providing activity guide information.

According to various embodiments, when several restrictions such as limit of a calculation capacity of the electronic device 100 or lack of power of a battery occur, the processor 120 may perform at least one of analysis of a pattern (e.g., determination of an activity engagement level to which activity information pertains), determination of a delivery time point of activity guide information, or adjustment of contents of activity guide information through an electronic device connected to the outside, a cloud server, or a specific server and may output a performance result received from the corresponding external device.

Figure 6:
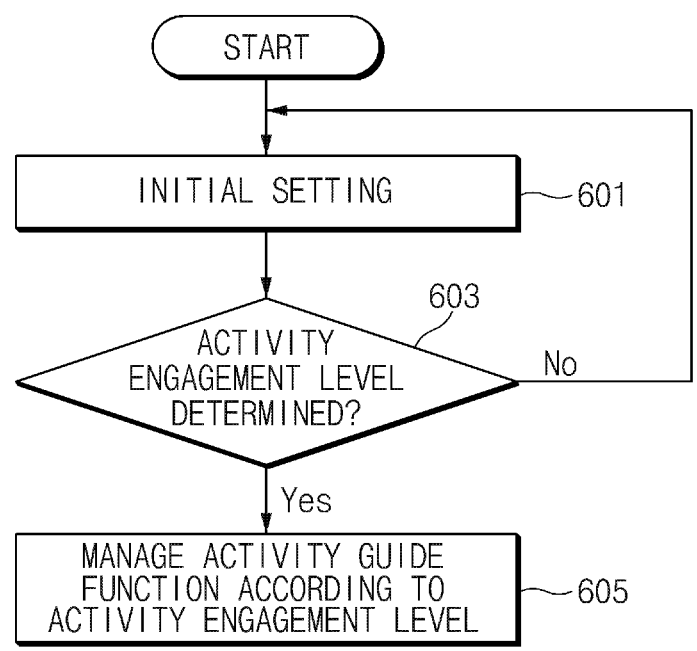
FIG. 6 is a view illustrating a method for providing activity guide information according to an embodiment.

FIG. 6 is a view illustrating a method for providing activity guide information according to an embodiment.

Referring to FIG. 6, in operation 601, the electronic device 100 (e.g., the processor 120) may perform a basic setting operation (e.g., an operation during an initial stage of use of a program or an initial time period of reuse of an initialized program). For example, the processor 120 of the electronic device 100 may enter a basic setting state if a program related to a user function of the present disclosure is installed and an input event related to basic setting is received. In relation to the basic setting operation, the processor 120 may be connected to the electronic device 100 or an external electronic device 1202 (e.g., a wearable device or various OT devices that may collect sensing information) to collect sensor information and obtain activity information from the sensor information. Further, the processor 120 may set a goal setting value from the user. In this regard, the processor 120 may provide a screen interface related to setting of a goal. In the basic setting operation, the processor 120 may analyze an activity pattern of the user by using the obtained activity information of the user, may create activity guide information by which a set goal may be achieved based on the analyzed contents, and may determine an output time point of the activity guide information.

The initial state of performance of a guide program may include a process of determining an activity engagement level while providing specific activity guide information in a process of the user using an activity guide information providing program for a specific time period or a specific number of times or more. The above-mentioned basic setting process may be defined as a default or may be adjusted according to selection of the user. For example, the basic setting process, for example, may include a process of managing a process until specific days (e.g., 14 days) passes after initial performance of a program. According to various embodiments, a time period in the basic setting process may be differently defined based on personal information (e.g., an age, a job, a normal amount of exercise input by the user, or a sex) of the user. Further, according to various embodiments, the time period in the basic setting process may be flexibly managed according to a program participation level of the user. For example, if a program participation level for days (or a week) of the user is a specific value or less (or more), a longer time period may be defined as a basic setting period. Further, if a program participation level for days (or a week) of the user is a specific value or more (or less), a shorter time period may be defined as a basic setting period. In the basic setting operation, if a specific time period passes, the processor 120 may determine an activity engagement level based on activity information during a specific time period. The processor 120 may provide guide information, activity induction information, and the like for a program in the basic setting operation.

In operation 603, the processor 120 may identify whether the activity engagement level has been determined. When the activity engagement level has not been determined, the processor 120 branches to operation 601 to perform the following operations again.

When the activity engagement level has been determined, the processor 120 may manage an activity guide function according to an activity engagement level in operation 605. For example, the processor 120 may determine a specific activity engagement level according to a program participation level of the user. According to an embodiment, the processor 120 may determine an activity engagement level as low, medium, and high according to a program engagement level in the basic setting process. For example, if the user manages a program for 3 days, 7 days, or 10 days of 14 days (e.g., sets an everyday goal and acts for attainment of a goal of a specific reference value or more), the activity engagement level may be defined as low, medium, and high according to a use time period. According to various embodiments, the above-mentioned activity engagement level may be differently applied according to personal information of the user. For example, even for the same use time period for the program, an activity engagement level of the user who is relatively old may be higher than an activity engagement level of the user who is relatively young.

The processor 120 may analyze a goal attainment degree for a goal input by the user with reference to the determined activity engagement level, and then, at a specific time interval (e.g., with reference to another time periods, such as in real time, daily, weekly, and monthly). Based on this, the processor 120 may predict whether a goal set by the user will be attained in a specific time period. For example, the processor 120 may convert past program use histories (or use histories in the basic setting process) of one or more users, may perform clustering, and may calculate a prediction rate for the possibility of attainment of a goal with reference to an average use history of the clustered groups.

According to various embodiments, the processor 120 may provide activity guide information based on a pattern of the day in which the set goal is attained. The processor 120 may compare a past goal attainment pattern of a user (or a plurality of users) and an attainment pattern for a recent specific time period to provide a difference therebetween. For example, the processor 120 may provide activity guide information for attainment of a goal if n % or more (or less) of the goal is attained for a recent specific time period. Further, the processor 120 may analyze a goal attainment frequency for a specific time period and a trend, and may provide activity guide information according to the analysis result.

According to an embodiment, the processor 120 may output activity guide information indicating that a goal of the user has to be increased if the user attains about twice or more of the goal set by the user for a specific time period.

Further, the processor 120 may output activity guide information that recommends lowering of a goal if the set goal attainment degree is a half.

According to various embodiments, the processor 120, for example, may output activity guide information of the contents related to a mistake if the prompt goal fails after the goal continues to be attained during a week. When a goal is attained after the goal continues to fail for a week, the processor 120 may output activity guide information including contents on the fact. In the above-mentioned function, the electronic device 100 may be provided with information related to a past history of the user through a server or the like. Further, the electronic device 100 may provide activity, pattern analysis information, and the like to the server for provision of a past history of the user.

Figure 7:
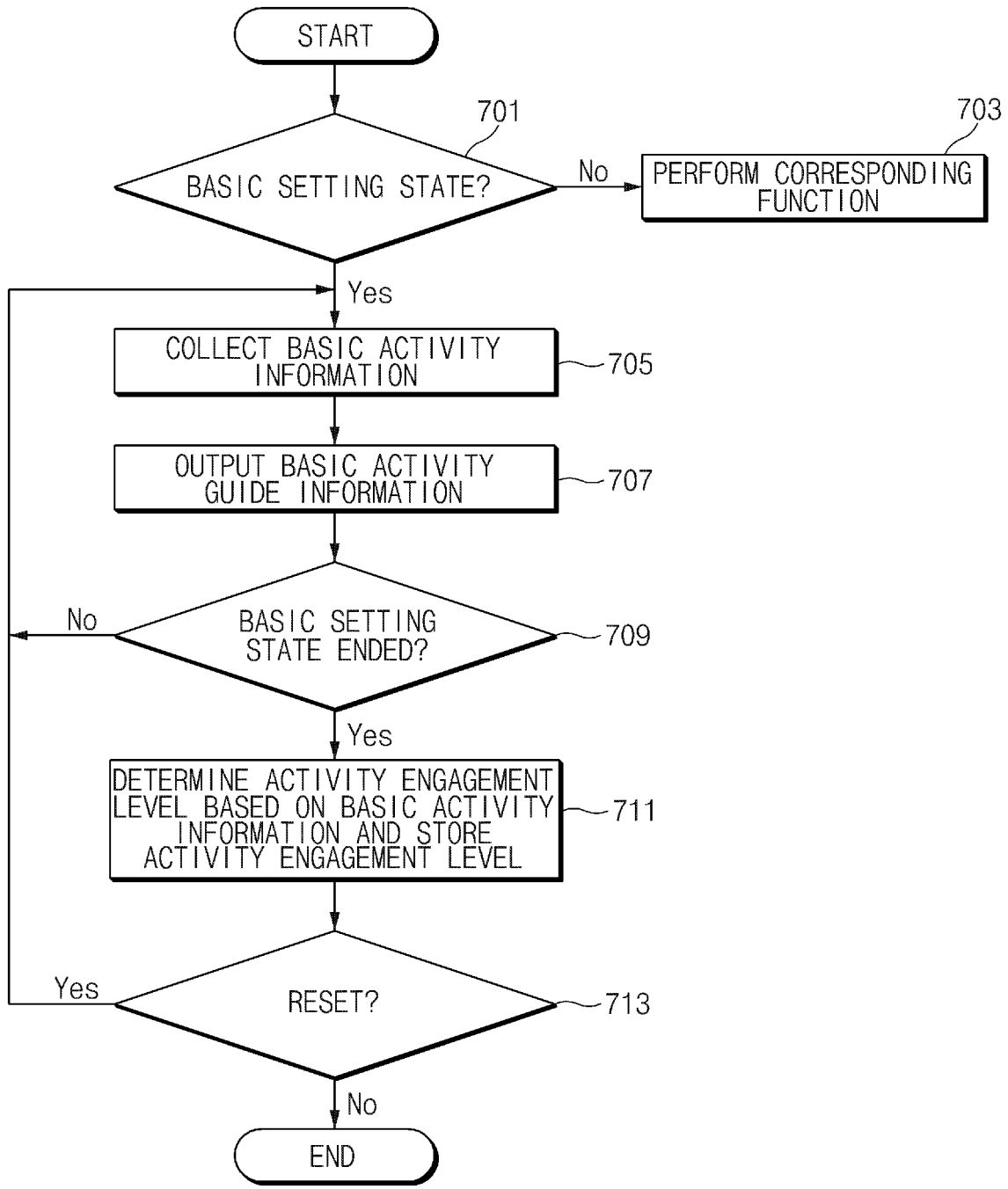
FIG. 7 is a view illustrating a basic setting method of a method for providing activity guide information according to an embodiment.

FIG. 7 is a view illustrating a basic setting method of a method for providing activity guide information according to an embodiment.

Referring to FIG. 7, in relation to a basic setting method, if an input event related to management of the electronic device 100 occurs, in operation 701, the electronic device (e.g., the processor 120) may identify whether the occurring input event is an input event related to start of a basic setting state. In the case of the event is not related to the start of the basic setting state, in operation 703, the processor 120 may process a function corresponding to the kind of an input event. The event related to the start of the basic setting state, for example, may include an input event to install an activity guide information providing program and request initial execution of the program, an input event to select a basic setting menu, and an input event to request initialization of the program.

If an input event related to start of the basic setting state occurs, in operation 705, the processor 120 may collect basic activity information. The basic activity information may include information on a time zone in which sensor information of a specific value or more is collected, the kind of sensor information, a non-collection time zone for sensor information, or a time zone in which sensor information of a specific value or less is collected In operation 707, the processor 120 may create and output basic activity guide information according to the collected activity information. For example, the processor 120 may analyze a pattern of basic activity information. The processor 120 may analyze a stored reference pattern and a pattern based on the basic activity information to identify to which reference pattern based on the basic activity information corresponds. The processor 120 may detect the corresponding reference pattern, and may select the basic activity guide information mapped with the corresponding reference pattern. The processor 120 may output the selected basic activity guide information through the display 160 or the input/output interface 150.

According to various embodiments, the processor 120 may provide activity guide information according to the activity engagement level. For example, the processor 120 classifies the user activity engagement level into onboarding, low, medium, and high, and provides a goal set by the user or exercise information or a progress state performed for a short time period (e.g., several days or one to two weeks) in an initial stage (basic setting state) after the start of the program.

According to various embodiments, the contents of provision of the activity guide information may vary when the program currently executed by the user is started just before (e.g., the case of basic setting) and according to whether the program has been consistently used for a specific time period (e.g., an activity engagement level). For example, the processor 120 may restrict output of a message that is expected to reduce an engagement level of the user in the basic setting state. For example, in the initial stage (e.g., the basic setting) of the program, the processor 120 may monitor a state of the user and provide the fact. Further, the processor 120 may relatively reduce a frequency of a message, such as exertion or induction of participation in the basic setting state. Then, the basic setting may correspond to an onboarding timing.

In operation 709, the processor 120 may identify whether an event related to ending of the basic setting state is satisfied. For example, the processor 120 may identify whether a specific time period passes, in relation to the basic setting. Further, in relation to the basic setting function, the processor 120 may identify occurrence of an input event to indicate whether sensor information of a specific amount or more has been collected, whether basic activity guide information has been output a specific number of times or more, and whether a basic setting state ends. When a condition related to the ending of the basic setting state is not satisfied, the processor 120 branches to an operation that is prior to operation 705 to perform the following operations again. If the condition related to the ending of the basic setting state is satisfied, in operation 711, the processor 120 may determine an activity engagement level based on the basic activity information and store the determined activity engagement level.

In operation 713, the processor 120 may identify whether a resetting condition for the basic setting is satisfied. The resetting condition, for example, may be a condition in which an input event to initialize the user function or request the basic setting occurs. When there is no resetting, the processor 120 may complete the basic setting function. If the resetting condition occurs, the processor 120 may branch to an operation that is prior to operation 705 to perform the following operations again.

Figure 8:
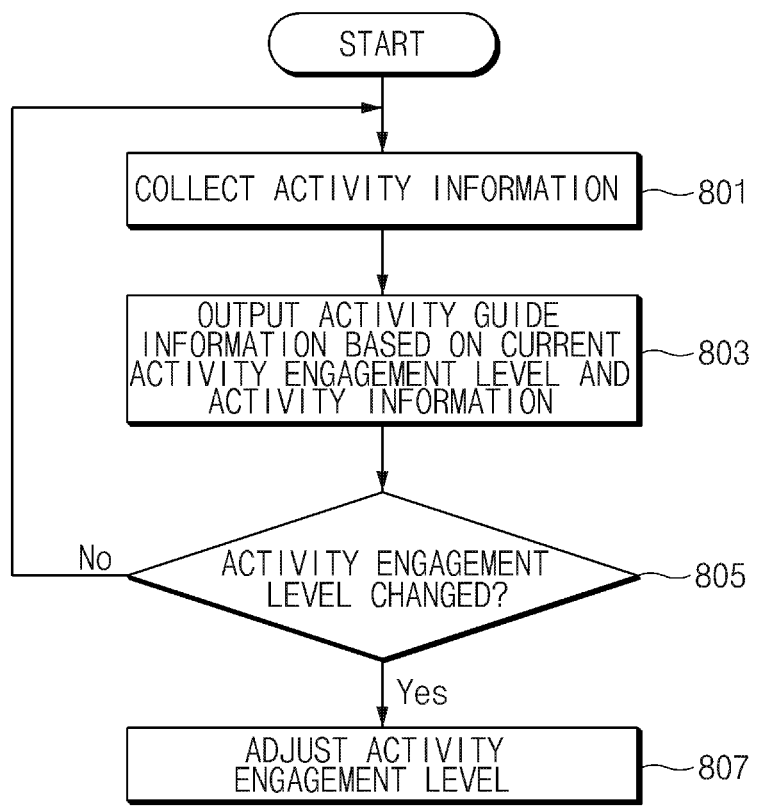
FIG. 8 is a view illustrating a method for adjusting an activity engagement level according to an embodiment.

FIG. 8 is a view illustrating a method for adjusting an activity engagement level according to an embodiment.

Referring to FIG. 8, in relation to the method for adjusting an activity engagement level, in operation 801, the electronic device (e.g., the processor 120) may collect activity information. For example, the processor 120 may collect activity information while classifying sensor information corresponding to a motion of a specific value or more and sensor information corresponding to a motion of less than a specific value, among the sensor information collected by the sensor 140.

In operation 803, the processor 120 may output activity guide information based on the set activity engagement level and activity information. For example, the processor 120 may extract a pattern by analyzing activity information during a specific time range that is prior from the current time point. The processor 120 may detect specific patterns that are the same or similar to the extracted pattern from the stored reference patterns. The processor 120 may output activity guide information mapped with the detected pattern. According to various embodiments, the processor 120 may calculate an attainment prediction degree for a goal set by the user based on the detected pattern. The processor 120 may output activity guide information set according to the attainment prediction degree. In this operation, the processor 120 may differently output at least one of whether activity guide information has been output, an output timing, an output cycle, the number of outputs, and output contents of the activity guide information according to an activity engagement level or a time point at which the activity guide information is created.

In operation 805, the processor 120 may identify an activity engagement level change condition based on the collected activity information. For example, the processor 120 may extract a pattern corresponding to the collected activity information, and may determine which activity engagement level the extracted pattern corresponds to. The processor 120 may determine that the activity engagement level change condition is satisfied when the extracted pattern is different from the activity engagement level. Further, the processor 120 may identify a duration for which the extracted pattern is different from the activity engagement level is maintained, or the number of times by which the extracted pattern is different from the activity engagement level. The processor 120 may determine that the activity engagement level change condition is satisfied if the duration or the number of times in a situation in which the extracted pattern is different from the activity engagement level is a specific value or more.

When the activity engagement level change condition is satisfied, in operation 807, the processor 120 may adjust the activity engagement level based on the activity information. For example, the processor 120 may lower or raise the activity engagement level based on the activity information. For example, when the activity engagement level is mid and the extracted pattern of the activity information in relation of the change of the activity engagement level is a high pattern, the activity engagement level may be changed to high. Further, when the extracted pattern is a low pattern in relation to the change of the activity engagement degree, the activity engagement level may be changed to low. As the activity engagement level is changed, the processor 120 may change the kind of activity guide information that is to be output. As described above with reference to FIG. 3 and the like, the contents, the number of outputs, the output cycle, and the output time point of the activity guide information may differently defined according to the activity engagement level.

If the activity engagement level change condition is not satisfied, the processor 120 is branched to an operation before operation 801 to perform the following operations again.

According to various embodiments, although it has been described that the activity guide function is performed after the performance of the basic setting operation, various embodiments of the present disclosure are not limited thereto. For example, the activity guide information providing program of the present disclosure may provide activity guide information according to various situations based on the activity guide function without managing the basic setting period. In this regard, the electronic device may determines the activity engagement level as a default, and may change the activity engagement level according to activity information (or an action pattern) of the user. In this operation, the electronic device 100 may change the activity engagement level in unit of a first time period (in real time or in unit of one hour) during a specific time period, and may change the activity engagement level in unit of a second time period (e.g., in unit of a day, in unit of a week, or in unit of a month) after a specific time period passes. The electronic device creates activity guide information according to the participation level of the current activity information with reference to the changed activity engagement level, and may output the created activity guide information. In the output process, the electronic device 100 may set at least one of whether the activity guide information is output, and the output time point, the number of outputs, the output cycle, and the output contents of the activity guide information as an activity guide parameter, and may output any one of the various pieces of activity guide information according to the adjustment of the activity guide parameter.

Figure 9:
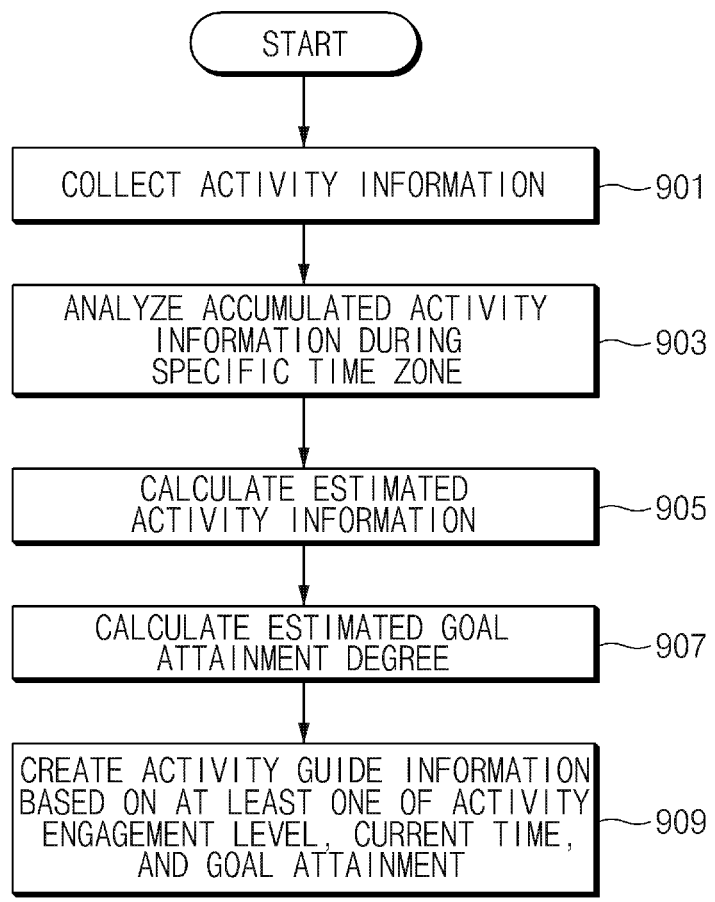
FIG. 9 is a view illustrating a method for creating activity guide information according to an embodiment.

FIG. 9 is a view illustrating a method for creating activity guide information according to an embodiment.

Referring to FIG. 9, in relation to the method for creating activity guide information, in operation 901, the electronic device (e.g., the processor 120) may collect activity information by using the sensor 140. For example, the processor 120 may collect sensor information in real time or at a specific cycle. The processor 120 may classify the sensor information into sensor information corresponding to a motion of a specific value or more and sensor information corresponding ab motion of a specific value or less. Further, the processor 120 may collect information on a time at which sensor information is not collected. The processor may collect activity information corresponding to the sensor information, the time at which the sensor information is not collected, and the like.

In operation 903, the processor 120 may analyze accumulated activity information during a specific time zone (e.g., the window). For example, the processor 120 may analyze the accumulated activity information during a specific time period (e.g., 6 hours) that is prior to the current time point. The processor 120, for example, may process a zone in which sensor information is not collected, a zone in which sensor information corresponding to a specific value or more is collected, and the like in a graph form, and may extract a pattern for the accumulated activity information.

In operation 905, the processor 120 may calculate activity estimated information. The processor 120 may detect a pattern that is the same as or similar to the extracted pattern (e.g., an activity pattern for 6 hours) from the reference patterns. In this regard, the electronic device 100 may store various reference patterns. The reference patterns, for example, may include pattern information of various time bands. For example, the reference patterns may include pattern information from 6 a.m. to 12 p.m. or 6 a.m. to 5:59 a.m. of the next day. The processor 120 may use activity information collection time band information in relation to detection of a similar pattern. For example, the processor 120 may detect patterns that are the same as or similar to each other in a time band that is the same as a time band in which the extracted pattern is analyzed, from the reference patterns. The processor 120 may calculate activity estimated information based on pattern information in the remaining time bands of the reference pattern if the same or similar pattern is detected.

In operation 907, the processor 120 may calculate estimated goal attainment degree. For example, the processor 120 may calculate whether a goal will be attained or which degree of the goal may be attained, based on the goal set by the user, the activity information, and the activity estimated information. According to an embodiment, the processor 120 may calculate a pattern related to attainment of a goal set by the user from the reference patterns (e.g., the activity patterns when the goal is attained). Here, the electronic device 100 may store information on the reference patterns for attaining the set goal values. If the reference pattern related to the attainment of the goal is detected, the processor 120 may calculate a concordance degree or a difference degree by comparing pattern information used in the activity estimated information and the reference pattern. The processor 120 may determine that an estimated goal attainment degree is low when the activity estimated information is lower than the reference pattern, and may determine that the estimated goal attainment degree is high when the activity estimated information is close to or higher than the reference pattern.

In operation 909, the processor 120 may create activity guide information based on at least one of an activity engagement level, a current time, and an estimated goal attainment degree. For example, the processor 120 may create information such as exertion, maintenance of the current state, motivation, delivery of the current state for the user based on the analyzed information. For example, the processor 120 combines one or more of an analysis result for real-time monitoring information or a goal attainment form (attained, unattained, or the like) of the user to create activity guide information (e.g., a notification, a guide, additional information, or a chart).

For example, when the estimated goal attainment degree is high, the processor 120 may output activity guide information that hints that attainment of the goal may be estimated. Then, activity guide information of different contents may be created according to a case in which the current activity time period is significantly smaller than the goal completion setting time period (e.g., 30 minutes) and a case in which the current activity time period is close to the goal completion setting time period (e.g., 1 hour and 50 minutes). For example, the processor 120 may create activity guide information of contents that guide the user to do well when the current activity time period is smaller than the goal completion setting time period to output the created activity guide information. When the current activity time period is close to the goal completion setting time period, the processor 120 may create activity guide information that guides the user that the user has been doing well and perfect attainment of the goal is possible if the user does activity a little further to output the activity guide information.

According to various embodiments, the processor 120 may make the contents or the output cycle of the activity guide information output according to the activity engagement level different. For example, the processor 120 may create and output activity guide information of contents that compliments the participation level of the user when the activity engagement level is low, and may create and output activity guide information of contents that induces a further activity for attainment of a goal of the user when the activity engagement level is high.

According to various embodiments, the processor 120 may add a change without providing a message at a specific time when the same performance result for the program is repeated. For example, the processor 120 may give a displacement time period at more random than a conventionally provided time interval or a specific time period without providing an analysis or activity guide information at a specific time to output the activity guide information. Based on this, the processor 120 may give an effect of preventing the user from feeling bored in the use of the program by changing the prediction of the output of the activity guide information.

According to various embodiments, the processor 120 may deliver different contents for different time bands in which the activity guide information is delivered. For example, the processor 120 may consider time delivery windows (time bands in which activity guide information is to be provided, for example, a morning time band and an afternoon time band). The processor 120 may classify the time windows based on the activity information of the user, such as a morning time band, of the day unit set to deliver activity guide information, which shows an ignition motion (first morning movement) and an afternoon time band in which the activity of the user is active, and may provide different pieces of information for respective windows (e.g., a morning time band: deliver summary information until the previous day and provide related activity guide information).

According to various embodiments, the processor 120 may use one or more of the enumerated elements to create or select the activity guide information that will be delivered to the user.

Figure 10:
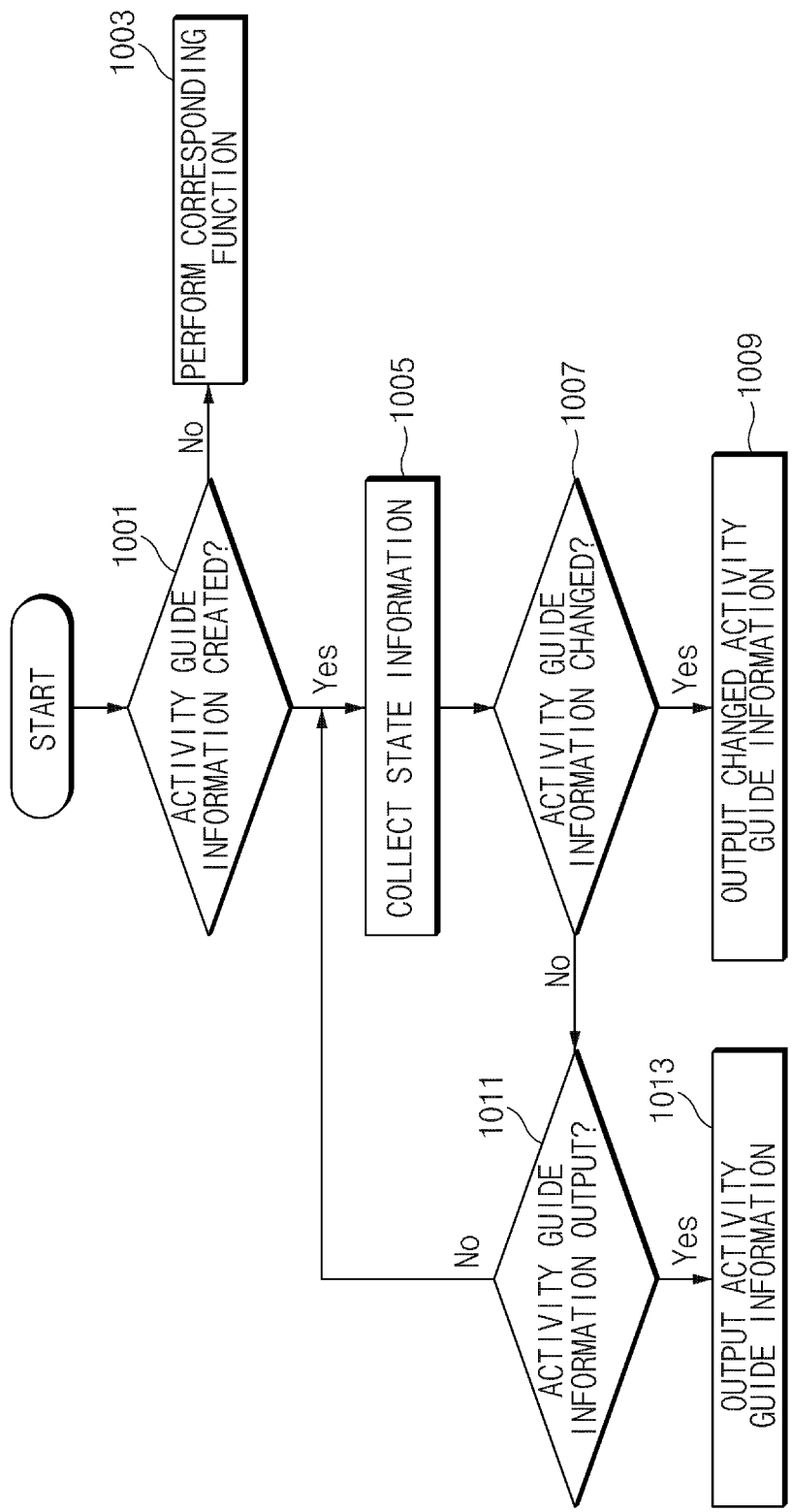
FIG. 10 is a view illustrating a method for outputting activity guide information according to an embodiment.

FIG. 10 is a view illustrating a method for outputting activity guide information according to an embodiment.

Referring to FIG. 10, in relation to the method for adjusting an activity engagement level, in operation 1001, the electronic device (e.g., the processor 120) may collect activity information. When activity guide information is not created, in operation 1003, the processor 120 may perform a specific function. For example, the processor 120 may collect activity information.

In operation 1005, the processor 120 may collect situation information (e.g., state information, motion information of the electronic device, or specific information) of the electronic device 100. For example, the processor 120 may determine whether the current state is an active state or an inactive state according to whether the electronic device 110 moves. The processor 120 may determine that the current state is an active state when there is a motion of a specific value or more (e.g., a motion is determined based on sensor information of a sensor included in the electronic device), and may determine that the current state is an inactive state when there is a motion of a specific value or less or there is no motion.

In operation 1007, the processor 120 may identify whether the activity guide information change condition is satisfied based on the state information. For example, the processor 120 may determine that the activity guide information change condition is satisfied when the electronic device 100 is maintained for a specific time period or more in an inactive state. Further, the processor 120 may determine that the activity guide information change condition is satisfied when the electronic device 100 is maintained for a specific time period or more in an inactive state and then is changed to an active state. According to various embodiments, the processor may determine that the activity guide information change condition is satisfied if the electronic device 100 is in an active state at a time point at which the activity guide information is output.

When the activity guide information change condition is satisfied, in operation 1009, the processor 120 changes the activity guide information and may output the changed activity guide information through at least one of the display 160 and the input/output interface 150. For example, the processor 120 may perform a control to output specific audio information through a screen of the display 160 and an audio device. According to various embodiments, the processor 120 may omit output of activity guide information if an output state is in an active state if the activity guide information is created and an output time point comes. When the contents of the activity guide information include contents that induce activity, the processor 120 may perform a control to output activity guide information of contents that complements state of an activity because the user starts an image activity.

According to various embodiments, the processor 120 may output activity guide information after changing information such that the contents have relatively positive contents when the user outputs the activity guide information in a current active state (or a state in which the user moves). When the user outputs activity guide information in the current inactive state, the processor 120 may output activity guide information after changing information such that the information has relatively negative contents. According to various embodiments, the processor 120 may determine a provision time point of the activity guide information and contents based on a progress based on a progress degree according to a goal attainment progress degree (e.g., 50%, 60%, 90%, or 95%).

When the activity guide information change condition is not satisfied, in operation 1011, the processor 120 may identify whether the activity guide information output condition is satisfied. If the activity guide information output condition is not satisfied, the processor 120 is branched to an operation before operation 1005 to perform the following operations again.

As described above, in the activity guide information that is delivered to the user, at least one of the number and interval of deliveries of message, a specific time period set by the user, or a time at which the program of the user may be performed may be adjusted based on whether the program is executed at an initial stage and a participation level of the program. The processor 120 may determine a time, such as morning, afternoon, evening, or sleeping, as a message delivery time and may identify whether the corresponding time has come. According to an embodiment, the processor 120 may identify whether the current time is a time at which the user acts actively and whether a day in which a goal was attained or almost attained has come. According to various embodiments, the processor 120 may determine a message that is suitable for a situation of the user if a time point at which the activity guide information is delivered is determined.

According to various embodiments, the processor 120 may make a time point at which the activity guide information is provided according to the activity engagement level. For example, when the program is executed at an initial stage, the processor 120 may induce interests in the program by frequently providing information. When the program performance participation level is relatively low, the processor 120 may excessively frequently provide the active guide information while making the activity guide information time point different as compared with another participation level so that the number of provisions of the message may be lowered such that the user does not feel inconvenient. Meanwhile, as the performance participation level increases relatively, the processor 120 may induce attainment of the goal by frequently providing information on the program performance situation or the goal attainment degree.

When the activity guide information output condition is not satisfied, in operation 1013, the processor 120 may output the activity guide information.

According to various embodiments, a method for providing activity guide information according to an embodiment includes collecting activity information on a user corresponding to an electronic device by using a sensor, creating an amount of activity of the user or an activity engagement level for a specific goal by using the activity information, adjusting at least one of an output time point, an output cycle, the number of outputs, or the output contents of the activity guide information for the user to an activity guide parameter at least based on the amount of activity or the activity engagement level, and providing the activity guide information created by using the adjusted activity guide information parameter through an output device.

According to various embodiments, the method may further include adjusting the activity guide parameter at least further based on the situation information.

According to various embodiments, the providing of the activity guide information includes determining whether the current state is a motion state or a non-motion state, and outputting specific activity guide information corresponding to the determined state.

According to various embodiments, a method for providing activity guide information according to an embodiment includes collecting sensor information, collecting activity information based on at least one of collection of the sensor information or a size of the sensor information, creating activity guide information that is to be output for the activity information based on a set goal, and outputting at least one of an output time point, an output cycle, and a number of outputs of the activity guide information is differently output based on at least one of a motion state of the electronic device, an activity engagement level set according to a program participation level, and a current time.

According to various embodiments, the outputting of the at least one includes making the output cycle of the activity guide information relatively short when the activity engagement level is relatively high, and making the output cycle of the activity guide information relatively long when the activity engagement level is relatively low.

According to various embodiments, the outputting of the at least one includes making the number of outputs of the activity guide information relatively large when the activity engagement level is relatively high, and making the number of outputs of the activity guide information relatively small when the activity engagement level is relatively low.

According to various embodiments, the outputting of the at least one includes omitting output of the activity guide information if the current motion state is a motion state, and outputting the activity guide information if the current motion state is a non-motion state for a specific time period.

According to various embodiments, the outputting of the at least one includes outputting activity guide information of different contents according to a time band to which a current time pertains.

According to various embodiments, the outputting of the at least one includes changing contents of the activity guide information and outputting the changed activity guide information when activity guide information that is to be output has the same contents as previously output activity guide information.

According to various embodiments, the method may further include determining a program engagement level based on activity information during a basic setting period of the program, and storing the determined activity engagement level according to the program engagement level.

According to various embodiments, the method may further include adjusting the activity engagement level according to a degree of repetitions of the activity information.

According to various embodiments, the adjusting of the activity engagement level includes decreasing the activity engagement level when a size of the activity information is maintained at a specific value or less for a specific time period, and increasing the activity engagement level when a size of the activity information is maintained at a specific value or more for a specific time period.

According to various embodiments, the creating of the activity guide information includes analyzing a pattern of the activity information, detecting a pattern at least a part of which is similar or the same, by comparing the analyzed pattern and stored reference patterns, calculating estimated activity information with reference to the detected pattern, calculating a target attainment degree by comparing the estimated activity information and the goal, and determining contents of the activity guide information based on the calculated goal attainment degree.

Figure 11:
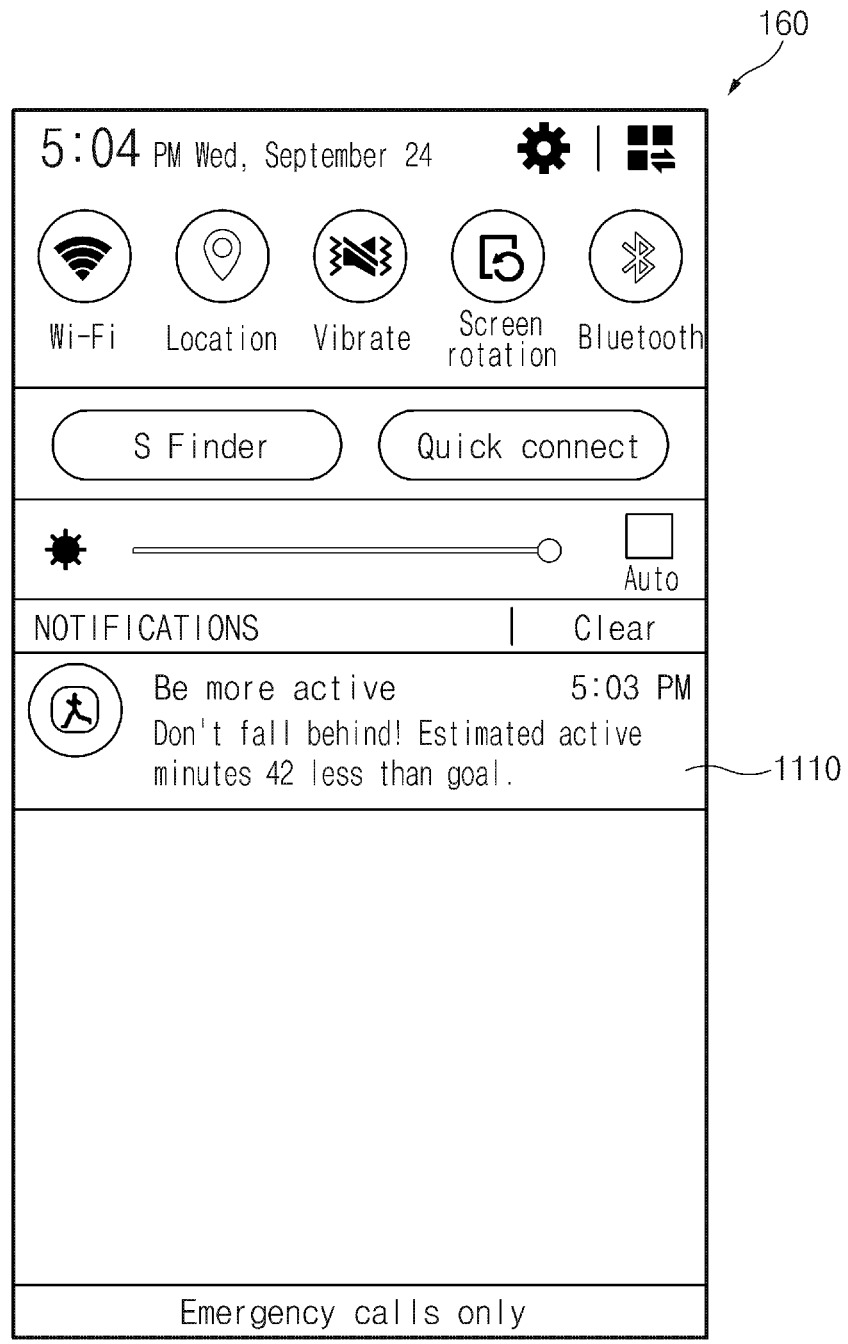
FIG. 11 is an example of a screen interface related to output of activity guide information according to an embodiment.

FIG. 11 is an example of a screen interface related to output of an activity guide information according to an embodiment.

Referring to FIG. 11, as illustrated, the display 160 of the electronic device 100 may output the activity guide information 1110. For example, the electronic device 100 may output a message screen according to a user input or specific setting through the display 160. The message screen, for example, may be a screen including at least one message related to management of the electronic device 100.

The activity guide information 110, for example, may be provided in a notification form through the display 160 of the electronic device. The notification may be activity guide information on progress of a goal. A goal achievement possibility and an expected degree of progress may be calculated by analyzing an active time progress of the past user, and then the activity guide information 1110 correspond thereto may be output. In the illustrated drawings, the process 120 predicts that the attainment of the goal is impossible and calculates an expected active time, and then indicates that a difference from the goal of the user is 42 minutes.

As described above, the electronic device 100 may allow the user to interactively manage information with the electronic device by selecting a program progress state or a reminder function based on the pattern analysis contents of the user at a suitable time point to accomplish a goal established by the user based on the collected activity information of the user, inducing the program performer to participate in the program through a long term.

The method for providing activity guide information of the electronic device may include an operation of setting a goal through an application, an operation of obtaining action state information of the user with a sensor of a portable device of the user, an operation of creating analysis information on action state information of the user based on the set goal, an operation of determining one or more of a provision time point, contents, and the number of the information that is provided to the user based on the analyzed information, and an operation of providing the determined information through the portable device of the user.

The analyzed information may include action pattern information of the user related to the set goal. The action pattern information of the user may include one or more of a user engagement level, a progress pattern, a goal attainment pattern, an overachieving/underachieving pattern, an anomaly defection in goal attainment.

Figure 12:
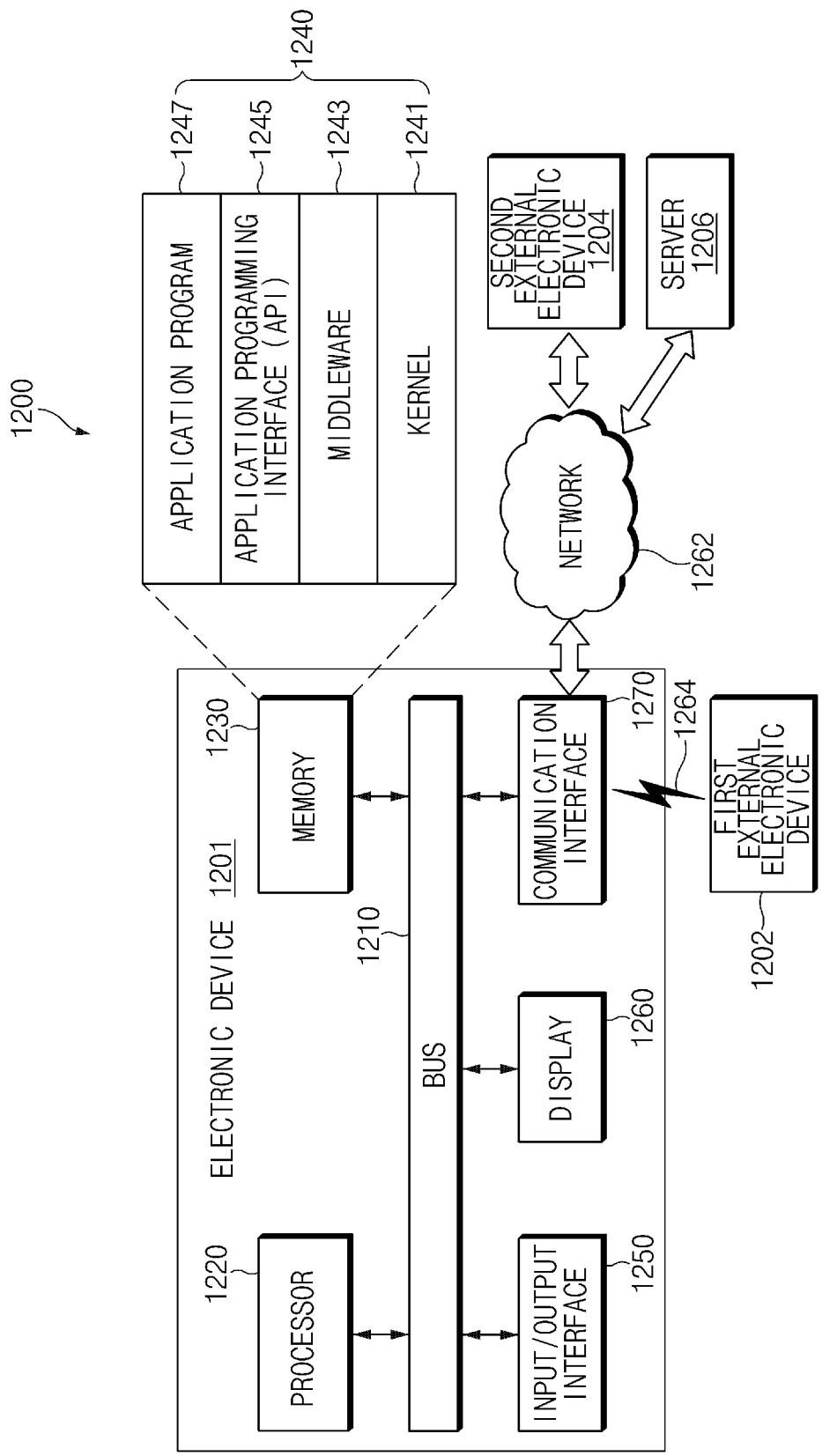
FIG. 12 is a block diagram illustrating a configuration of an electronic device in a network environment according to an embodiment.

FIG. 12 is a block diagram illustrating a configuration of an electronic device in a network environment according to an embodiment.

Referring to FIG. 12, in various embodiments, an electronic device 1201 and a first external electronic device 1202, a second external electronic device 1204, or a server 1206 may connect with each other through a network 1262 or local-area communication 1264. The electronic device 1201 may include a bus 1210, a processor 1220, a memory 1230, an input and output interface 1250, a display 1260, and a communication interface 1270. In various embodiments, at least one of the components may be omitted from the electronic device 1201, or other components may be additionally included in the electronic device 1201.

The bus 1210 may be, for example, a circuit which connects the components 1220 to 1270 with each other and transmits a communication signal (e.g., a control message and/or data) between the components.

The processor 1220 may include one or more of a central processing unit (CPU), an application processor (AP), or a communication processor (CP). For example, the processor 1220 may perform calculation or data processing about control and/or communication of at least another of the components of the electronic device 1201.

The memory 1230 may include a volatile and/or non-volatile memory. The memory 1230 may store, for example, a command or data associated with at least another of the components of the electronic device 1201. According to an embodiment, the memory 1230 may store software and/or a program 1240. The program 1240 may include, for example, a kernel 1241, a middleware 1243, an application programming interface (API) 1245, and/or an least one application program 1247 (or "at least one application"), and the like. At least part of the kernel 1241, the middleware 1243, or the API 1245 may be referred to as an operating system (OS).

The kernel 1241 may control or manage, for example, system resources (e.g., the bus 1210, the processor 1220, or the memory 1230, and the like) used to execute an operation or function implemented in the other programs (e.g., the middleware 1243, the API 1245, or the application program 1247). Also, as the middleware 1243, the API 1245, or the application program 1247 accesses a separate component of the electronic device 1201, the kernel 1241 may provide an interface which may control or manage system resources.

The middleware 1243 may play a role as, for example, a go-between such that the API 1245 or the application program 1247 communicates with the kernel 1241 to communicate data.

Also, the middleware 1243 may process one or more work requests, received from the application program 1247, in order of priority. For example, the middleware 1243 may assign priority which may use system resources (the bus 1210, the processor 1220, or the memory 1230, and the like) of the electronic device 1201 to at least one of the at least one application program 1247. For example, the middleware 1243 may perform scheduling or load balancing for the one or more work requests by processing the one or more work requests in order of the priority assigned to the at least one of the at least one application program 1247.

The API 1245 may be, for example, an interface in which the application program 1247 controls a function provided from the kernel 1241 or the middleware 1243. For example, the API 1245 may include at least one interface or function (e.g., a command) for file control, window control, image processing, or text control, and the like.

The input and output interface 1250 may play a role as, for example, an interface which may transmit a command or data input from a user or another external device to another component (or other components) of the electronic device 1201. Also, input and output interface 1250 may output an instruction or data received from another component (or other components) of the electronic device 1201 to the user or the other external device.

The display 1260 may include, for example, a liquid crystal display (LCD), a light emitting diode (LED) display, an organic LED (OLED) display, a microelectromechanical systems (MEMS) display, or an electronic paper display. The display 1260 may display, for example, a variety of content (e.g., text, images, videos, icons, or symbols, and the like) to the user. The display 1260 may include a touch screen, and may receive, for example, touch, gesture, proximity, or a hovering input using an electronic pen or part of a body of the user.

The communication interface 1270 may establish communication between, for example, the electronic device 1201 and an external device (e.g., a first external electronic device 1202, a second external electronic device 1204, or a server 1206). For example, the communication interface 1270 may connect to a network 1262 through wireless communication or wired communication and may communicate with the external device (e.g., the second external electronic device 1204 or the server 1206).

The wireless communication may use, for example, at least one of long term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM), and the like as a cellular communication protocol. Also, the wireless communication may include, for example, local-area communication 1264. The local-area communication 1264 may include, for example, at least one of wireless-fidelity (Wi-Fi) communication, Bluetooth (BT) communication, near field communication (NFC), or global navigation satellite system (GNSS) communication, and the like.

An MST module may generate a pulse based on transmission data using an electromagnetic signal and may generate a magnetic field signal based on the pulse. The electronic device 1201 may output the magnetic field signal to a point of sales (POS) system. The POS system may restore the data by detecting the magnetic field signal using an MST reader and converting the detected magnetic field signal into an electric signal.

The GNSS may include, for example, at least one of a global positioning system (GPS), a Glonass, a Beidou navigation satellite system (hereinafter referred to as "Beidou"), or a Galileo (i.e., the European global satellite-based navigation system) according to an available area or a bandwidth, and the like. Hereinafter, the "GPS" used herein may be interchangeably with the "GNSS". The wired communication may include at least one of, for example, universal serial bus (USB) communication, high definition multimedia interface (HDMI) communication, recommended standard 232 (RS-232) communication, or plain old telephone service (POTS) communication, and the like. The network 1262 may include a telecommunications network, for example, at least one of a computer network (e.g., a local area network (LAN) or a wide area network (WAN)), the Internet, or a telephone network.

Each of the first and second external electronic devices 1202 and 1204 may be the same as or different device from the electronic device 1201. According to an embodiment, the server 1206 may include a group of one or more servers. According to various embodiments, all or some of operations executed in the electronic device 1201 may be executed in another electronic device or a plurality of electronic devices (e.g., the first external electronic device 1202, the second external electronic device 1204, or the server 1206). According to an embodiment, if the electronic device 1201 should perform any function or service automatically or according to a request, it may request another device (e.g., the first external electronic device 1202, the second external electronic device 1204, or the server 106) to perform at least part of the function or service, rather than executing the function or service for itself or in addition to the function or service. The other electronic device (e.g., the first external electronic device 1202, the second external electronic device 1204, or the server 1206) may execute the requested function or the added function and may transmit the executed result to the electronic device 1201. The electronic device 1201 may process the received result without change or additionally and may provide the requested function or service. For this purpose, for example, cloud computing technologies, distributed computing technologies, or client-server computing technologies may be used.

Figure 13:
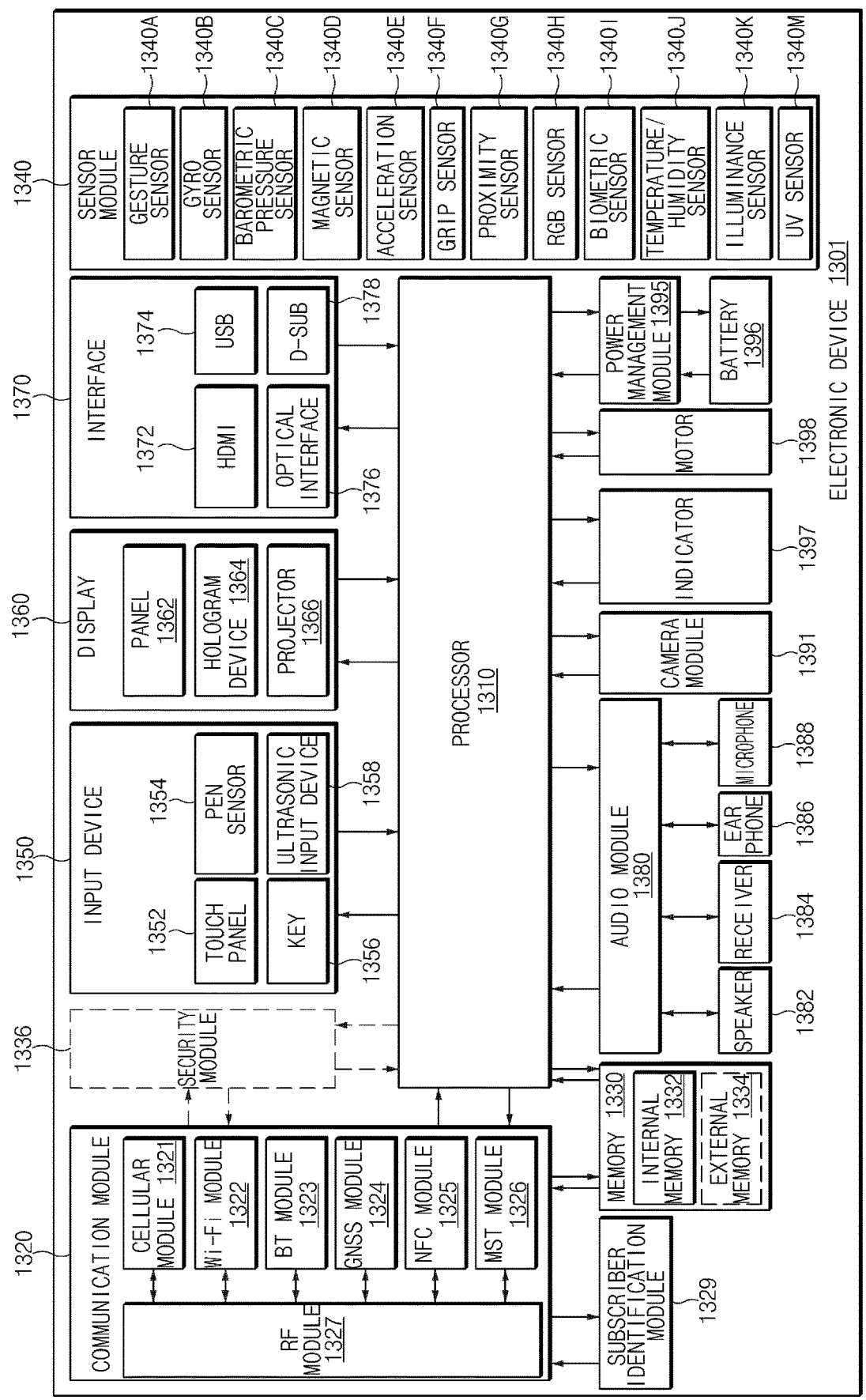
FIG. 13 is a block diagram illustrating a configuration of an electronic device according to various embodiments.

FIG. 13 is a block diagram illustrating a configuration of an electronic device according to various embodiments.

Referring to FIG. 13, the electronic device 1301 may include, for example, all or part of an electronic device 1201 shown in FIG. 12. The electronic device 1301 may include one or more processors 1310 (e.g., application processors (APs)), a communication module 1320, a subscriber identification module (SIM) 1329, a memory 1330, a security module 1336, a sensor module 1340, an input device 1350, a display 1360, an interface 1370, an audio module 1380, a camera module 1391, a power management module 1395, a battery 1396, an indicator 1397, and a motor 1398.

The processor 1310 may drive, for example, an operating system (OS) or an application program to control a plurality of hardware or software components connected thereto and may process and compute a variety of data. The processor 1310 may be implemented with, for example, a system on chip (SoC). According to an embodiment, the processor 1310 may include a graphic processing unit (GPU) (not shown) and/or an image signal processor (not shown). The processor 1310 may include at least some (e.g., a cellular module 1321) of the components shown in FIG. 13. The processor 1310 may load a command or data received from at least one of other components (e.g., a non-volatile memory) into a volatile memory to process the data and may store various data in a non-volatile memory.

The communication module 1320 may have the same or similar configuration to a communication interface 1270 of FIG. 12. The communication module 1320 may include, for example, the cellular module 1321, a wireless-fidelity (Wi-Fi) module 1322, a Bluetooth (BT) module 1323, a global navigation satellite system (GNSS) module 1324 (e.g., a GPS module, a Glonass module, a Beidou module, or a Galileo module), a near field communication (NFC) module 1325, an MST module 1326, and a radio frequency (RF) module 1327.

The cellular module 1321 may provide, for example, a voice call service, a video call service, a text message service, or an Internet service, and the like through a communication network. According to an embodiment, the cellular module 1321 may identify and authenticate the electronic device 1301 in a communication network using the SIM 1329 (e.g., a SIM card). According to an embodiment, the cellular module 1321 may perform at least part of functions which may be provided by the processor 1310. According to an embodiment, the cellular module 1321 may include a communication processor (CP).

The Wi-Fi module 1322, the BT module 1323, the GNSS module 1324, the NFC module 1325, or the MST module 1326 may include, for example, a processor for processing data transmitted and received through the corresponding module. According to various embodiments, at least some (e.g., two or more) of the cellular module 1321, the Wi-Fi module 1322, the BT module 1323, the GNSS module 1324, the NFC module 1325, or the MST module 1326 may be included in one integrated chip (IC) or one IC package.

The RF module 1327 may transmit and receive, for example, a communication signal (e.g., an RF signal). Though not shown, the RF module 1327 may include, for example, a transceiver, a power amplifier module (PAM), a frequency filter, or a low noise amplifier (LNA), or an antenna, and the like. According to another embodiment, at least one of the cellular module 1321, the Wi-Fi module 1322, the BT module 1323, the GNSS module 1324, the NFC module 1325, or the MST module 1326 may transmit and receive an RF signal through a separate RF module.

The SIM 1329 may include, for example, a card which includes a SIM and/or an embedded SIM. The SIM 1329 may include unique identification information (e.g., an integrated circuit card identifier (ICCID)) or subscriber information (e.g., an international mobile subscriber identity (IMSI)).

The memory 1330 (e.g., a memory 1230 of FIG. 12) may include, for example, an embedded memory 1332 or an external memory 1334. The embedded memory 1332 may include at least one of, for example, a volatile memory (e.g., a dynamic random access memory (DRAM), a static RAM (SRAM), a synchronous dynamic RAM (SDRAM), and the like), or a non-volatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory or a NOR flash memory, and the like), a hard drive, or a solid state drive (SSD)).

The external memory 1334 may include a flash drive, for example, a compact flash (CF), a secure digital (SD), a micro-SD, a mini-SD, an extreme digital (xD), a multimedia car (MMC), or a memory stick, and the like. The external memory 1334 may operatively and/or physically connect with the electronic device 1301 through various interfaces.

The secure module 1336 may be a module which has a relatively higher secure level than the memory 1330 and may be a circuit which stores secure data and guarantees a protected execution environment. The secure module 1336 may be implemented with a separate circuit and may include a separate processor. The secure module 1336 may include, for example, an embedded secure element (eSE) which is present in a removable smart chip or a removable SD card or is embedded in a fixed chip of the electronic device 1301. Also, the secure module 1336 may be driven by an OS different from the OS of the electronic device 1301. For example, the secure module 1336 may operate based on a java card open platform (JCOP) OS.

The sensor module 1340 may measure, for example, a physical quantity or may detect an operation state of the electronic device 1301, and may convert the measured or detected information to an electric signal. The sensor module 1340 may include at least one of, for example, a gesture sensor 1340A, a gyro sensor 1340B, a barometer sensor 1340C, a magnetic sensor 1340D, an acceleration sensor 1340E, a grip sensor 1340F, a proximity sensor 1340G, a color sensor 1340H (e.g., red, green, blue (RGB) sensor), a biometric sensor 13401, a temperature/humidity sensor 1340J, an illumination sensor 1340K, or an ultraviolet (UV) sensor 1340M. Additionally or alternatively, the sensor module 1340 may further include, for example, an e-nose sensor (not shown), an electromyography (EMG) sensor (not shown), an electroencephalogram (EEG) sensor (not shown), an electrocardiogram (ECG) sensor (not shown), an infrared (IR) sensor (not shown), an iris sensor (not shown), and/or a fingerprint sensor (not shown), and the like. The sensor module 1340 may further include a control circuit for controlling at least one or more sensors included therein. According to various embodiments, the electronic device 1301 may further include a processor configured to control the sensor module 1340, as part of the processor 1310 or to be independent of the processor 1310. While the processor 1310 is in a sleep state, the electronic device 1301 may control the sensor module 1340.

According to various embodiments, the sensor module may include a blood pressure monitor, a blood glucose monitor, a PPG, an ECG, an EMG, an EEG, an oxygen saturation measurement sensor, a skin moisture measurement sensor, an obesity measurer, and a body temperature sensor. The biometric information sensor for recognizing a biometric feature of the user may include a fingerprint sensor, an iris recognition sensor, a face recognition sensor, a hand shape recognition sensor, a hand vessel recognition sensor, a voice recognition sensor, and a signature recognition sensor, and a camera, an IR camera, a touch sensor, and a microphone may be used.

Among them, the health sensor is a sensor that collects one or more biometric signals from the user. For example, the health sensor collects raw data for measuring one or more of the blood pressure, the blood flow, the heart rate (HRM(Heart Rate Measurement), HRV), the body temperature, the respiration rate, the oxygen saturation, the heart/lung sound, the blood sugar, the waist circumference, the height, the weight, the body fat, the calorie consumption, the brain wave, the voice, the skin resistance, the electromyogram, the electrocardiogram, the walk, the ultrasonic image, the sleep state, the facial expression (face), the pupil dilation, and the eye blinkering. Biometric feature information may be extracted by analyzing the biometric signal. For example, a pulse wave obtained through a heart rate variability (HRV) may be a biometric signal, and primary biometric feature information, such as an average heart rate and a heartbeat distribution may be obtained by analyzing the biometric signal and secondary biometric feature information, such as a higher stress state or a blood vessel aging degree may be obtained by processing the biometric feature information. The health sensor may simply output the collected user biometric signal, and may analyze the biometric signal through a processor device embedded together with the sensor to output the biometric feature information. Accordingly, the biometric signal collected through the health sensor may be delivered to a processor coupled to a sensor and a processor of a local device in which a sensor device is embedded to be analyzed, and may be used to produce biometric feature information. For example, a mobile phone in which an ECG sensor is embedded may be used, or a wrist witch in which a PPG sensor is embedded may be used.

As another example, a biometric signal collected by a HRV sensor embedded in an ear clip may be delivered to a wrist watch device or a smartphone, and the device that received the biometric signal may extract biometric feature information. The extracted information may be delivered to the device that extracted the biometric feature information or one or more other devices. If a smartphone extracted the biometric feature information, the biometric feature information may be delivered to a display of the wrist watch device and to the ear clip through a voice. According to various embodiments, a signal of a touch sensor, a signal of a key input detection sensor, an impact detection sensor, a vibration detection sensor, or a signal for a wired/wireless device connection may be detected. One sensor may sense two or more pieces of information. For example, the acceleration sensor may measure the motion and the number of steps of the user at the same time. In another example, the PPG sensor may be utilized as a biometric information sensor for measuring the heart rates and stress of the user, and may be utilized as a proximity sensor based on the amount of received light. As another example, the ECG signal may recognize the emotion, the heart rate, and the heart rate variability-(HRV) of the user through analysis of a cardiogram of the user, and may be used for authentication for distinguishing the user.

As an embodiment, the sensor may be always driven while the electronic device is powered on. As another embodiment, the sensor may be driven according to an input (e.g., a key input, a button input, a GUI input, recognition of a gesture) of the user. As another embodiment, if one sensor is operated, another sensor associated with the sensor may be automatically driven. According to various embodiments, the sensor may be embedded in the electronic device, and may be embedded in another device or may be installed in an external environment (e.g., an interior, an exterior, a building, or a base station).

The input device 1350 may include, for example, a touch panel 1352, a (digital) pen sensor 1354, a key 1356, or an ultrasonic input device 1358. The touch panel 1352 may use at least one of, for example, a capacitive type, a resistive type, an infrared type, or an ultrasonic type. Also, the touch panel 1352 may further include a control circuit. The touch panel 1352 may further include a tactile layer and may provide a tactile reaction to a user.

The (digital) pen sensor 1354 may be, for example, part of the touch panel 1352 or may include a separate sheet for recognition. The key 1356 may include, for example, a physical button, an optical key, or a keypad. The ultrasonic input device 1358 may allow the electronic device 1301 to detect a sound wave using a microphone (e.g., a microphone 1388) and to verify data through an input tool generating an ultrasonic signal.

The display 1360 (e.g., a display 1260 of FIG. 12) may include a panel 1362, a hologram device 1364, or a projector 1366. The panel 1362 may include the same or similar configuration to the display 160 or 1260. The panel 1362 may be implemented to be, for example, flexible, transparent, or wearable. The panel 1362 and the touch panel 1352 may be integrated into one module. The hologram device 1364 may show a stereoscopic image in a space using interference of light. The projector 1366 may project light onto a screen to display an image. The screen may be positioned, for example, inside or outside the electronic device 1301. According to an embodiment, the display 1360 may further include a control circuit for controlling the panel 1362, the hologram device 1364, or the projector 1366.

The interface 1370 may include, for example, a high-definition multimedia interface (HDMI) 1372, a universal serial bus (USB) 1374, an optical interface 1376, or a D-subminiature 1378. The interface 1370 may be included in, for example, a communication interface 170 or 1270 shown in FIG. 2 or 12. Additionally or alternatively, the interface 1370 may include, for example, a mobile high definition link (MHL) interface, an SD card/multimedia card (MMC) interface, or an infrared data association (IrDA) standard interface.

The audio module 1380 may convert a sound and an electric signal in dual directions. At least part of components of the audio module 1380 may be included in, for example, an input and output interface 1250 (or a user interface) shown in FIG. 12. The audio module 1380 may process sound information input or output through, for example, a speaker 1382, a receiver 1384, an earphone 1386, or the microphone 1388, and the like.

The camera module 1391 may be a device which captures a still image and a moving image. According to an embodiment, the camera module 1391 may include one or more image sensors (not shown) (e.g., a front sensor or a rear sensor), a lens (not shown), an image signal processor (ISP) (not shown), or a flash (not shown) (e.g., an LED or a xenon lamp).

The power management module 1395 may manage, for example, power of the electronic device 1301. According to an embodiment, though not shown, the power management module 1395 may include a power management integrated circuit (PMIC), a charger IC or a battery or fuel gauge. The PMIC may have a wired charging method and/or a wireless charging method. The wireless charging method may include, for example, a magnetic resonance method, a magnetic induction method, or an electromagnetic method, and the like. An additional circuit for wireless charging, for example, a coil loop, a resonance circuit, or a rectifier, and the like may be further provided. The battery gauge may measure, for example, the remaining capacity of the battery 1396 and voltage, current, or temperature thereof while the battery 1396 is charged. The battery 1396 may include, for example, a rechargeable battery or a solar battery.

The indicator 1397 may display a specific state of the electronic device 1301 or part (e.g., the processor 1310) thereof, for example, a booting state, a message state, or a charging state, and the like. The motor 1398 may convert an electric signal into mechanical vibration and may generate vibration or a haptic effect, and the like. Though not shown, the electronic device 1301 may include a processing unit (e.g., a GPU) for supporting a mobile TV. The processing unit for supporting the mobile TV may process media data according to standards, for example, a digital multimedia broadcasting (DMB) standard, a digital video broadcasting (DVB) standard, or a mediaFlo™ standard, and the like.

Each of the above-mentioned elements of the electronic device according to various embodiments of the present disclosure may be configured with one or more components, and names of the corresponding elements may be changed according to the type of the electronic device. The electronic device according to various embodiments of the present disclosure may include at least one of the above-mentioned elements, some elements may be omitted from the electronic device, or other additional elements may be further included in the electronic device. Also, some of the elements of the electronic device according to various embodiments of the present disclosure may be combined with each other to form one entity, thereby making it possible to perform the functions of the corresponding elements in the same manner as before the combination.

Figure 14:
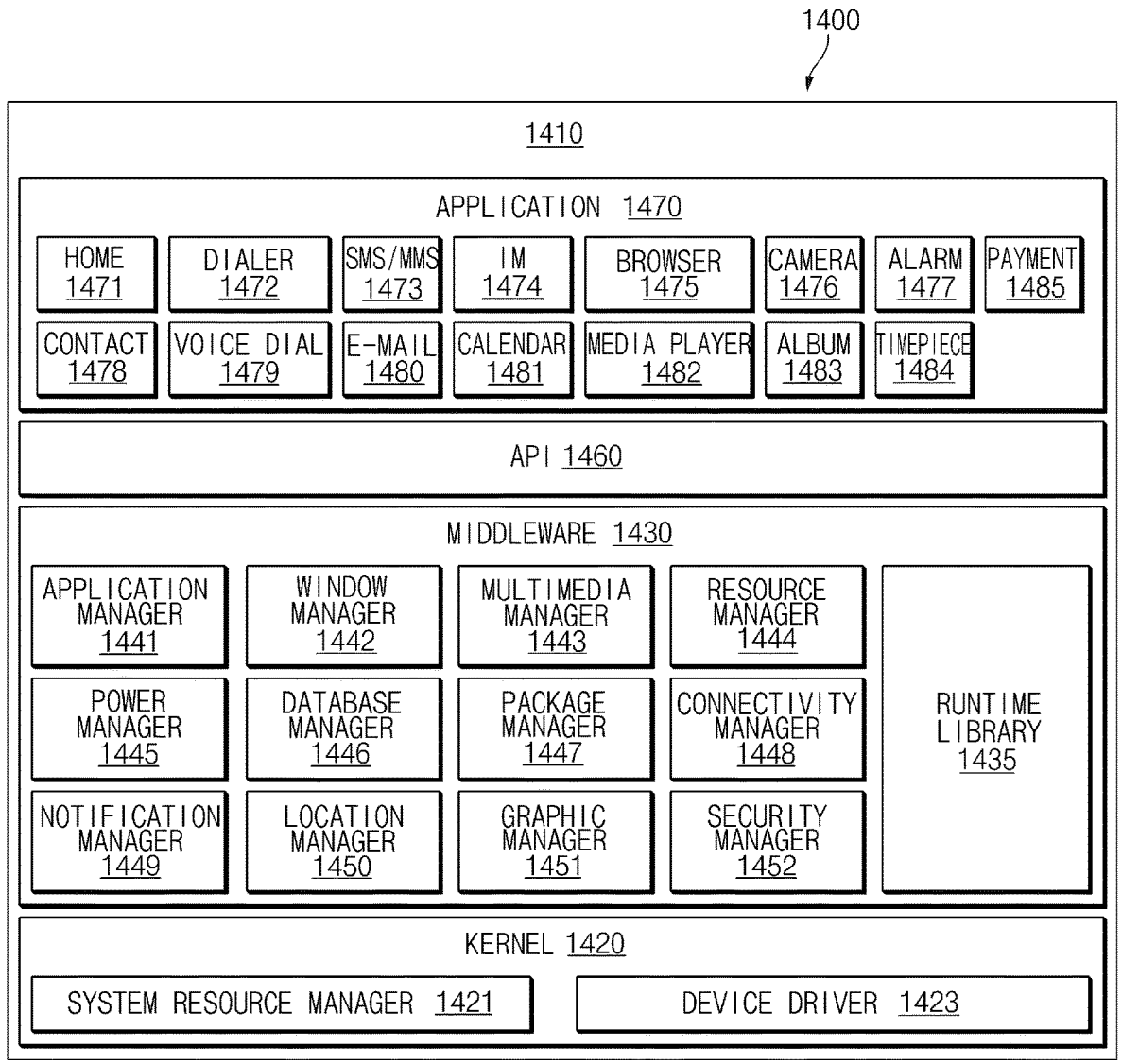
FIG. 14 is a block diagram illustrating a configuration of a program module according to various embodiments.

FIG. 14 is a block diagram illustrating a configuration of a program module according to various embodiments.

According to an embodiment, the program module 1410 (e.g., a program 1240 of FIG. 12) may include an operating system (OS) for controlling resources associated with an electronic device (e.g., an electronic device 1201 of FIG. 12) and/or various applications (e.g., an application program 1247 of FIG. 12) which are executed on the OS. The OS may be, for example, Android, iOS, Windows, Symbian, Tizen, or Bada, and the like.

The program module 1410 may include a kernel 1420, a middleware 1430, an application programming interface (API) 1460, and/or an application 1470. At least part of the program module 1410 may be preloaded on the electronic device, or may be downloaded from an external electronic device (e.g., a first external electronic device 1202, a second external electronic device 1204, or a server 1206, and the like of FIG. 12).

The kernel 1420 (e.g., a kernel 1241 of FIG. 12) may include, for example, a system resource manager 1421 and/or a device driver 1423. The system resource manager 1421 may control, assign, or collect, and the like system resources. According to an embodiment, the system resource manager 1421 may include a process management unit, a memory management unit, or a file system management unit, and the like. The device driver 1423 may include, for example, a display driver, a camera driver, a Bluetooth (BT) driver, a shared memory driver, a universal serial bus (USB) driver, a keypad driver, a wireless-fidelity (Wi-Fi) driver, an audio driver, or an inter-process communication (IPC) driver.

The middleware 1430 (e.g., a middleware 1243 of FIG. 12) may provide, for example, functions the application 1470 needs in common, and may provide various functions to the application 1470 through the API 1460 such that the application 1470 efficiently uses limited system resources in the electronic device. According to an embodiment, the middleware 1430 (e.g., the middleware 1243) may include at least one of a runtime library 1435, an application manager 1441, a window manager 1442, a multimedia manager 1443, a resource manager 1444, a power manager 1445, a database manager 1446, a package manager 1447, a connectivity manager 1448, a notification manager 1449, a location manager 1450, a graphic manager 1451, a security manager 1452, or a payment manager 1454.

The runtime library 1435 may include, for example, a library module used by a compiler to add a new function through a programming language while the application 1470 is executed. The runtime library 1435 may perform a function about input and output management, memory management, or an arithmetic function.

The application manager 1441 may manage, for example, a life cycle of at least one of the application 1470. The window manager 1442 may manage graphic user interface (GUI) resources used on a screen of the electronic device. The multimedia manager 1443 may determine a format utilized for reproducing various media files and may encode or decode a media file using a codec corresponding to the corresponding format. The resource manager 1444 may manage source codes of at least one of the application 1470, and may manage resources of a memory or a storage space, and the like.

The power manager 1445 may act together with, for example, a basic input/output system (BIOS) and the like, may manage a battery or a power source, and may provide power information utilized for an operation of the electronic device. The database manager 1446 may generate, search, or change a database to be used in at least one of the application 1470. The package manager 1447 may manage installation or update of an application distributed by a type of a package file.

The connectivity manager 1448 may manage, for example, wireless connection such as Wi-Fi connection or BT connection, and the like. The notification manager 1449 may display or notify events, such as an arrival message, an appointment, and proximity notification, by a method which is not disturbed to the user. The location manager 1450 may manage location information of the electronic device. The graphic manager 1451 may manage a graphic effect to be provided to the user or a user interface (UI) related to the graphic effect. The security manager 1452 may provide all security functions utilized for system security or user authentication, and the like. According to an embodiment, when the electronic device (e.g., an electronic device 100 or 1201 of FIG. 1 or 12) has a phone function, the middleware 1430 may further include a telephony manager (not shown) for managing a voice or video communication function of the electronic device.

The middleware 1430 may include a middleware module which configures combinations of various functions of the above-described components. The middleware 1430 may provide a module which specializes according to kinds of OSs to provide a differentiated function. Also, the middleware 1430 may dynamically delete some of old components or may add new components.

The API 1460 (e.g., an API 1245 of FIG. 12) may be, for example, a set of API programming functions, and may be provided with different components according to OSs. For example, in case of Android or iOS, one API set may be provided according to platforms. In case of Tizen, two or more API sets may be provided according to platforms.

The application 1470 (e.g., an application program 1247 of FIG. 12) may include one or more of, for example, a home application 1471, a dialer application 1472, a short message service/multimedia message service (SMS/MMS) application 1473, an instant message (IM) application 1474, a browser application 1475, a camera application 1476, an alarm application 1477, a contact application 1478, a voice dial application 1479, an e-mail application 1480, a calendar application 1481, a media player application 1482, an album application 1483, a clock application 1484, a health care application (e.g., an application for measuring quantity of exercise or blood sugar, and the like), or an environment information application (e.g., an application for providing atmospheric pressure information, humidity information, or temperature information, and the like), and the like.

According to an embodiment, the application 1470 may include an application (hereinafter, for better understanding and ease of description, referred to as "information exchange application") for exchanging information between the electronic device (e.g., the electronic device 1201 of FIG. 12) and an external electronic device (e.g., the first external electronic device 1202 or the second external electronic device 1204). The information exchange application may include, for example, a notification relay application for transmitting specific information to the external electronic device or a device management application for managing the external electronic device.

For example, the notification relay application may include a function of transmitting notification information, which is generated by other applications (e.g., the SMS/MMS application, the e-mail application, the health care application, or the environment information application, and the like) of the electronic device, to the external electronic device (e.g., the first external electronic device 1202 or the second external electronic device 1204). Also, the notification relay application may receive, for example, notification information from the external electronic device, and may provide the received notification information to the user of the electronic device.

The device management application may manage (e.g., install, delete, or update), for example, at least one (e.g., a function of turning on/off the external electronic device itself (or partial components) or a function of adjusting brightness (or resolution) of a display) of functions of the external electronic device (e.g., the first external electronic device 1202 or the second external electronic device 1204) which communicates with the electronic device, an application which operates in the external electronic device, or a service (e.g., a call service or a message service) provided from the external electronic device.

According to an embodiment, the application 1470 may include an application (e.g., the health card application of a mobile medical device) which is preset according to attributes of the external electronic device (e.g., the first external electronic device 1202 or the second external electronic device 1204). According to an embodiment, the application 1470 may include an application received from the external electronic device (e.g., the server 1206, the first external electronic device 1202, or the second external electronic device 1204). According to an embodiment, the application 1470 may include a preloaded application or a third party application which may be downloaded from a server. Names of the components of the program module 1410 according to various embodiments of the present disclosure may differ according to kinds of OSs.

According to various embodiments, at least part of the program module 1410 may be implemented with software, firmware, hardware, or at least two or more combinations thereof. At least part of the program module 1410 may be implemented (e.g., executed) by, for example, a processor (e.g., a processor 1220 of FIG. 12). At least part of the program module 1410 may include, for example, a module, a program, a routine, sets of instructions, or a process, and the like for performing one or more functions.

The terminology "module" used herein may mean, for example, a unit including one of hardware, software, and firmware or two or more combinations thereof. The terminology "module" may be interchangeably used with, for example, terminologies "unit", "logic", "logical block", "component", or "circuit", and the like. The "module" may be a minimum unit of an integrated component or a part thereof. The "module" may be a minimum unit performing one or more functions or a part thereof. The "module" may be mechanically or electronically implemented. For example, the "module" may include at least one of an application-specific integrated circuit (ASIC) chip, field-programmable gate arrays (FPGAs), or a programmable-logic device, which is well known or will be developed in the future, for performing certain operations.

According to various embodiments of the present disclosure, at least part of a device (e.g., modules or the functions) or a method (e.g., operations) may be implemented with, for example, instructions stored in computer-readable storage media which have a program module. When the instructions are executed by a processor, one or more processors may perform functions corresponding to the instructions. The computer-readable storage media may be, for example, a memory.

The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

Embodiments of the present disclosure described and shown in the drawings are provided as examples to describe technical content and help understanding but do not limit the present disclosure. Accordingly, it should be interpreted that besides the embodiments listed herein, all modifications or modified forms derived based on the technical ideas of the present disclosure are included in the present disclosure as defined in the claims, and their equivalents.

Modules or program modules according to various embodiments of the present disclosure may include at least one or more of the above-mentioned components, some of the above-mentioned components may be omitted, or other additional components may be further included. Operations executed by modules, program modules, or other components may be executed by a successive method, a parallel method, a repeated method, or a heuristic method. Also, some operations may be executed in a different order or may be omitted, and other operations may be added.

The invention claimed is:

1. A portable electronic device comprising:
a sensor configured to collect activity information;
a memory configured to store the collected activity information; and
a processor operatively connected to the sensor and the memory,
wherein the processor is configured to execute at least one instruction, causing the portable electronic device to:
collect the activity information for a user via the sensor,
determine an amount of user activity relevant to a specific goal or an activity engagement level for the specific goal, using the collected activity information,
adjust an activity guide parameter based on the amount of user activity or the activity engagement level, including at least one of a time point to output an activity guide information and a frequency at which to output the activity guide information,
analyze a previous active time progress of the user during an elapsed time within a basic setting period,
compare the previous active time progress with the specific goal for the basic setting period,
calculate a possibility that the specific goal will be achieved and a proportion of completion for the specific goal, based on the comparison of the previous active time progress with the specific goal, and
output the activity guide information according to the adjusted activity guide parameter including at least the adjusted frequency through an output device operatively connected to the processor, including the calculated proportion of completion,
wherein the processor is configured to:
identify situation information of the electronic device; and
adjust the frequency further based at least on the situation information,
wherein the activity guide information is output as a series of activity guide notifications,
wherein when the activity engagement level is greater than a first threshold, the activity guide notifications are output at a first frequency, and when the activity engagement level is less than or equal to the first threshold, the activity guide notifications are output at a second frequency less than the first frequency.

2. The electronic device of claim 1, wherein the processor is configured to:

determine a current state of the electronic device via the sensor, including whether the electronic device is moving or stationary and output the activity guide information according to the determined current state.

3. The electronic device of claim 1, wherein the processor is configured to:
output the activity guide information according to a time band of a day, to which a current time pertains.

4. The electronic device of claim 1, wherein the processor is configured to:
when the activity guide information to be output includes particular content identical with content included in previously output activity guide information, change the particular content of the activity guide information for output.

5. The electronic device of claim 1, wherein the at least one instruction is part of a executable program,
wherein the processor is configured to:
determine a program engagement level for the executable program based on a subset of the activity information collected during a basic setting period of the executable program, and
wherein the determined activity engagement level is stored according to the program engagement level.

6. The electronic device of claim 1, wherein the processor is configured to:
adjust the activity engagement level according to a degree of repetition indicated by the activity information.

7. The electronic device of claim 1, wherein the collected activity information includes a pattern, and the processor is configured to:
detect and identify the pattern by comparing the pattern with reference patterns stored in the memory,
calculate estimated activity information based at least in part on the detected pattern, and
calculate a goal attainment degree by comparing the estimated activity information and the specific goal,
wherein output content of the activity guide information is selected based at least in part on the calculated goal attainment degree.

8. A method in an electronic device for providing activity guide information, the method comprising:
collecting activity information on a user via a sensor;
determining, via a processor, an amount of user activity relevant to a specific goal or an activity engagement level for the specific goal, using the collected activity information;
adjusting an activity guide parameter based on the amount of user activity or the activity engagement level, including at least one of a time point to output the activity guide information and a frequency at which to output the activity guide information,
analyzing a previous active time progress of the user during an elapsed time within a basic setting period;
comparing the previous active time progress with the specific goal for the basic setting period;
calculating a possibility that the specific goal will be achieved and a proportion of completion for the specific goal, based on the comparison of the previous active time progress with the specific goal; and
outputting the activity guide information according to the adjusted activity guide parameter including at least the frequency through an output device operatively connected to the processor, wherein the activity guide information includes the calculated proportion of completion,
wherein the method further comprises:
adjusting the frequency further based at least on situation information of the electronic device,
wherein the activity guide information is output as a series of activity guide notifications,
wherein when the activity engagement level is greater than a first threshold, the activity guide notifications are output at a first frequency, and when the activity engagement level is less than or equal to the first threshold, the activity guide notifications are output at a second frequency less than the first frequency.

9. The method of claim 8, wherein the outputting of the activity guide information includes:
outputting the activity guide information according to a time band of a day, to which a current time pertains.

10. The method of claim 8, wherein the outputting of the activity guide information includes:
when activity guide information to be output includes particular content identical with content included in previously output activity guide information, changing the particular content of the activity guide information for output.

11. The method of claim 8, wherein the activity guide information is provided via an executable program, further comprising:
determining a program engagement level for the executable program based on a subset of the activity information collected during a basic setting period of the executable program; and
storing the activity engagement level determined according to the determined program engagement level.

12. The method of claim 8, further comprising:
adjusting the activity engagement level according to a degree of repetition indicated by the activity information.

13. The method of claim 8, wherein the collected activity information includes a pattern, and the determining of the activity guide information includes:
detecting and identifying the pattern by comparing the pattern with stored reference patterns;
calculating estimated activity information based at least in part on the identified pattern; and
calculating a goal attainment degree by comparing the estimated activity information and the specific goal,
wherein output content of the activity guide information is selected based at least in part on the calculated goal attainment degree.

* * * * *